(12) United States Patent
Neri et al.

(10) Patent No.: US 10,239,939 B2
(45) Date of Patent: *Mar. 26, 2019

(54) ANTI-ED-A IMMUNOCONJUGATES FOR INFLAMMATORY BOWEL DISEASE

(71) Applicant: PHILOGEN S.P.A., Siena (IT)

(72) Inventors: Giovanni Neri, Sovicille (IT); Kathrin Schwager, Zurich (CH); Melanie C. Ruzek, Cambridge, MA (US); Denise M. O'hara, Andover, MA (US); Jianqing Chen, Andover, MA (US)

(73) Assignee: PHILOGEN S.P.A., Siena (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,213

(22) Filed: Jun. 1, 2017

(65) Prior Publication Data

US 2018/0044408 A1    Feb. 15, 2018

Related U.S. Application Data

(63) Continuation of application No. 14/431,745, filed as application No. PCT/US2012/058574 on Oct. 3, 2012, now Pat. No. 9,695,232.

(51) Int. Cl.
| | |
|---|---|
| *C07K 16/18* | (2006.01) |
| *A61K 38/06* | (2006.01) |
| *A61K 39/395* | (2006.01) |
| *A61K 38/07* | (2006.01) |
| *A61K 38/08* | (2019.01) |
| *A61K 38/20* | (2006.01) |
| *A61K 47/68* | (2017.01) |
| *C07K 14/54* | (2006.01) |

(52) U.S. Cl.
CPC .............. *C07K 16/18* (2013.01); *A61K 38/06* (2013.01); *A61K 38/07* (2013.01); *A61K 38/08* (2013.01); *A61K 38/2066* (2013.01); *A61K 47/6843* (2017.08); *A61K 39/3955* (2013.01); *C07K 2317/565* (2013.01); *C07K 2317/622* (2013.01); *C07K 2317/626* (2013.01)

(58) Field of Classification Search
None
See application file for complete search history.

(56) References Cited

U.S. PATENT DOCUMENTS

| | | | |
|---|---|---|---|
| 5,368,854 | A | 11/1994 | Rennick |
| 5,420,012 | A | 5/1995 | Partanen et al. |
| 5,565,332 | A | 10/1996 | Hoogenboom et al. |
| 5,733,743 | A | 3/1998 | Johnson et al. |
| 5,858,657 | A | 1/1999 | Winter et al. |
| 5,859,205 | A | 1/1999 | Adair et al. |
| 5,871,907 | A | 2/1999 | Winter et al. |
| 5,872,215 | A | 2/1999 | Osbourne et al. |
| 5,885,793 | A | 3/1999 | Griffiths et al. |
| 5,932,214 | A | 8/1999 | Lobb et al. |
| 5,962,255 | A | 10/1999 | Griffiths et al. |
| 5,969,108 | A | 10/1999 | McCafferty et al. |
| 6,140,471 | A | 10/2000 | Johnson et al. |
| 6,172,197 | B1 | 1/2001 | McCafferty et al. |
| 6,225,447 | B1 | 5/2001 | Winter et al. |
| 6,291,650 | B1 | 9/2001 | Winter et al. |
| 6,492,160 | B1 | 12/2002 | Griffiths et al. |
| 6,521,404 | B1 | 2/2003 | Griffiths et al. |
| 7,148,202 | B2 | 12/2006 | Larocca |
| 7,968,685 | B2 | 6/2011 | Brack et al. |
| 8,222,377 | B2 | 7/2012 | Kaspar et al. |
| 8,263,041 | B2 | 9/2012 | Rybak et al. |
| 8,481,684 | B2 | 2/2013 | Rybak et al. |
| 8,404,814 | B2 | 3/2013 | Neri et al. |
| 8,679,488 | B2 | 3/2014 | Kaspar et al. |
| 9,181,347 | B2 | 11/2015 | Rybak et al. |
| 9,198,976 | B2 | 12/2015 | Lee et al. |
| 9,446,124 | B2 | 9/2016 | Kaspar et al. |
| 9,695,232 | B2 | 7/2017 | Neri et al. |
| 9,782,496 | B2 | 10/2017 | Corti et al. |
| 9,896,503 | B2 | 2/2018 | Rybak et al. |
| 2002/0187100 | A1 | 12/2002 | Rizzier et al. |
| 2003/0077589 | A1 | 4/2003 | Hess-Stumpp et al. |
| 2004/0185053 | A1 | 9/2004 | Govindan |
| 2006/0024724 | A1 | 2/2006 | Hussa et al. |
| 2006/0024725 | A1 | 2/2006 | Hussa et al. |
| 2006/0024757 | A1 | 2/2006 | Hussa et al. |

(Continued)

FOREIGN PATENT DOCUMENTS

| | | |
|---|---|---|
| CN | 101918443 | 12/2010 |
| EP | 0120694 | 10/1984 |

(Continued)

OTHER PUBLICATIONS

2016 Medicines in development for autoimmune diseases.*
Philogen 2013 Dekavil clinical trials.*
Goldsby, Immunology, 5th edition, 2003, pp. 82-84.*
Huston et al. Proc. Natl. Acad. Sci., 85(16):5879-5883, 1988.*
Bird et al Science, 242:243-246, 1988.*
Ward et al. Nature, 341:544-546, 1989.*
Rudikoff, et al. Proc. Natl. Acad. Sci. USA, 79(6):1979-1983, 1982.*
McCarthy and Hill J. Immunol. Methods, 251(1-2):137-149, 2001.*
Adams et al., "High affinity restricts the localization and tumor penetration of single-chain fv antibody molecules," Cancer Res., 61:4750-4755 (2001).
Aguyao et al., "Angiogenesis in acute and chronic leukemias and myelodysplastic syndromes," Blood, 96(6):2240-2245 (2000).

(Continued)

*Primary Examiner* — Bridget E Bunner
*Assistant Examiner* — Fozia Hamud
(74) *Attorney, Agent, or Firm* — Haley Guiliano LLP; James F. Haley, Jr.; Brian M. Gummow

(57) ABSTRACT

Specific binding members that bind the ED-A isoform of fibronectin for use in methods of treatment, diagnosis, detection and/or imaging of inflammatory bowel disease (IBD), and/or for use in delivery to the IBD tissue of a molecule conjugated to the specific binding member. The specific binding member may, for example, be conjugated to an immunosupressive or anti-inflammatory molecule, such as interleukin-10.

16 Claims, 7 Drawing Sheets

Specification includes a Sequence Listing.

(56) References Cited

U.S. PATENT DOCUMENTS

| | | |
|---|---|---|
| 2006/0115428 A1 | 6/2006 | Menrad et al. |
| 2006/0188501 A1 | 8/2006 | Homma et al. |
| 2007/0082879 A1 | 4/2007 | Goodman |
| 2007/0202044 A1 | 8/2007 | Goldenberg |
| 2008/0248038 A1 | 10/2008 | Corvinus et al. |
| 2009/0068106 A1 | 3/2009 | Corti et al. |
| 2010/0183506 A1 | 7/2010 | Neri et al. |
| 2010/0247541 A1 | 9/2010 | Rybak et al. |
| 2010/0260707 A1 | 10/2010 | Kaspar et al. |
| 2011/0250131 A1 | 10/2011 | Schwager |
| 2012/0244114 A1 | 9/2012 | Kaspar et al. |
| 2012/0251439 A1 | 10/2012 | Schwager |
| 2013/0309257 A1 | 11/2013 | Casi Giulio |
| 2015/0361161 A1 | 12/2015 | Neri et al. |
| 2016/0039920 A1 | 2/2016 | Casi et al. |
| 2016/0200789 A1 | 7/2016 | Hemmerle et al. |
| 2017/0183398 A1 | 6/2017 | Schwager |
| 2017/0298122 A1 | 10/2017 | Kaspar |

FOREIGN PATENT DOCUMENTS

| | | |
|---|---|---|
| EP | 0125023 | 11/1984 |
| EP | 0184187 | 6/1986 |
| EP | 0239400 | 9/1987 |
| EP | 0344134 | 5/1989 |
| EP | 0580859 | 2/1994 |
| EP | 0603735 | 6/1994 |
| GB | 2188638 A | 7/1924 |
| RU | 2280254 | 7/2006 |
| WO | WO-1992001047 | 1/1992 |
| WO | WO-1993011161 | 6/1993 |
| WO | WO-1994013804 | 6/1994 |
| WO | WO-2000034784 | 6/2000 |
| WO | WO-2001062298 | 8/2001 |
| WO | WO-2001083816 | 11/2001 |
| WO | WO-2002020563 | 3/2002 |
| WO | WO-2002406455 | 6/2002 |
| WO | WO-2002057290 | 7/2002 |
| WO | WO-2004000216 | 12/2003 |
| WO | WO-2004067038 | 8/2004 |
| WO | WO-2004094612 | 11/2004 |
| WO | WO-2005009366 | 2/2005 |
| WO | WO-2005066348 | 7/2005 |
| WO | WO-2005086612 | 9/2005 |
| WO | WO-2006026020 | 3/2006 |
| WO | WO-2006050834 | 5/2006 |
| WO | WO-2006119897 | 11/2006 |
| WO | WO-2007005608 | 1/2007 |
| WO | WO-2007128563 | 11/2007 |
| WO | WO-2008120101 | 10/2008 |
| WO | WO-2009013619 | 1/2009 |
| WO | WO-2009056268 | 5/2009 |
| WO | WO-2010078945 | 7/2010 |
| WO | WO-2010078950 | 7/2010 |
| WO | WO-2011015333 | 2/2011 |
| WO | WO-2013014149 | 1/2013 |

OTHER PUBLICATIONS

Allie, A search service for abbreviation / long form, p. 1, (Jun. 27, 2012).
Amit et al., "Three-dimensional structure of an antigen-antibody complex at 2.8 A resolution," Science, 233:747-753 (1986).
Andersen et al., "Recombinant protein expression for therapeutic applications," Current Opinion in Biotechnology 13:117-123 (2002).
Asadullah et al. (Pharmacology Reviews, (2003), 55, 245-269.
Astrof et al., "Direct test of potential roles of EIIIA and EIIIB alternatively spliced segments of fibronectin in physiological and tumor angiogenesis," Mol Cell Biol., 24:8662-8670 (2004).
Auerbach et al., "Angiogenesis assays: problems and pitfalls," Cancer Metastasis Rev., 19:167-172 (2000).
Bagshawe et al. (1991) Antibody, Immunoconjugates and Radiopharmaceuticals 4:915-922.

Ballard et al., "Vascular tenascin-C regulates cardiac endothelial phenotype and neovascularization," The FASEB Journal, 20(6):717-719 (2006).
Balza et al., "Transforming growth factor B regulates the levels of different fibronectin isoforms in normal human cultured fibroblasts," FEBS Letters, 228(1):42-44 (1988).
Batista et al., "The two membrane isoforms of human IgE assemble into functionally distinct B cell antigen receptors," J. Exp. Med., 184:2197-205 (1996).
Beguin et al., "Soluble CD23 and other receptors (CD4, CD8, CD25, CD71) in serum of patients with chronic lymphocytic leukemia," Leukemia., 7:2019-2025 (1993).
Berndorff et al., "Imaging of tumor angiogenesis using 99mTc-labeled human recombinant anti-ED-B fibronectin antibody fragments," J Nucl Med., 47:1707-1716 (2006).
Berndorff et al., "Radioimmunotherapy of solid tumors by targeting extra domain B fibronectin: identification of the best-suited radioimmunoconjugate," Clin Cancer Res., 11:7053s-7063s (2005).
Berndt et al., "Differential expression of tenascin-C splicing domains in urothelial carcinomas of the urinary bladder," Journal of Cancer Research and Clinical Oncology, 132:537-546 (2006).
Berndt et al., "Evidence of ED-B+ fibronectin synthesis in human tissues by nonradioactive RNA in situ hybridization Investigations on carcinoma (oral squamous cell and breast carcinoma), chronic inflammation (rheumatoid synovitis) and fibromatosis (Morbus Dupuytren),"Histochemistry and Cell Biology, 109:249-255 (1998).
Birchler et al., "Infrared photodetection for the in vivo localisation of phage-derived antibodies directed against angiogenic markers," Journal of Immunological Methods, 231:239-248 (1999).
Birchler et al., "Selective targeting and photocoagulation of ocular angiogenesis mediated by a phage-derived human antibody fragment," Nature Biotechnology, 17:984-988 (1999).
Bird et al., "Single-chain antigen-binding proteins," Science, 242:423-426 (1988).
Bootz et al., "Alternatively Spliced EDA Domain of Fibronectin Is a Target for Pharmacodelivery Applications in Inflammatory Bowel Disease," Inflammatory Bowel Disease, 21(8):1908-1917 (2015).
Borsi et al., "Expression of different tenascin isoforms in normal, hyperplastic and neoplastic human breast tissues," Int J. Cancer., 52:688-692 (1992).
Borsi et al., "Monoclonal Antibodies in the Analysis of Fibronectin Isoforms Generated by Alternative Splicing of mRNA Precursors in Normal and Transformed Human Cells," Journal of Cell Biology, 104:595-600 (1987).
Borsi et al., "Preparation of Phage Antibodies to the ED-A Domain of Human Fibronectin," Experimental Cell Research, 240:244-251 (1998).
Borsi et al., "Selective Targeting of Tumoral Vasculature: Comparison of Different Formats of an Antibody (L19) to the ED-B Domain of Fibronectin," International Journal of Cancer, 102:75-85 (2002).
Borsi et al., "The Alternative Splicing Pattern of the Tenascin-C Pre-mRNA Is Controlled by the Extracellular pH," Journal of Biological Chemistry, 270(11):6243-6245 (1995).
Borsi et al., "Transforming growth factor-P regulates the splicing pattern of fibronectin messenger RNA precursor," FEBS Letters, 261(1):175-178 (1990).
Bose et al, "Problems in using statistical analysis of replacement and silent mutations in antibody genes for determining antigen-driven affinity selection," Immunology, 116(2):172-183 (2005).
Brack et al., "Tumor-Targeting Properties of Novel Antibodies Specific to the Large Isoform of Tenascin-C," Clinical Cancer Research, 12(10):3200-3208 (2006).
Brenmoehl et al., "Evidence for a differential expression of fibronectin splice forms ED-A and ED-B in Crohn's disease (CD) mucosa," Int. J. Colorectal Dis., 22:611-623 (2007).
Brenmoehl et al., "Inflammation modulates fibronectin isoform expression in colonic lamina propria fibroblasts (CLPF)," Int. J. Colorectal Dis., 23:947-955 (2008).
Brown et al., "Tolerance of single, but not multiple, amino acid replacements in antibody VH CDR 2: a means of minimizing B cell wastage from somatic hypermutation?," Journal of Immunology, 3285-3291 (1996).

(56) References Cited

OTHER PUBLICATIONS

Burrows et al., "Up-regulation of endoglin on vascular endothelial cells in human solid tumors: implications for diagnosis and therapy," Clin Cancer Res., 1:1623-1634 (1995).
Carnemolla et al., "A Tumor-associated Fibronectin Isoform Generated by Alternative Splicing of Messenger RNA Precursors," Journal of Cell Biology, 108:1139-1148 (1989).
Carnemolla et al., "Enhancement of the antitumor properties of interleukin-2 by its targeted delivery to the tumor blood vessel extracellular matrix," Blood, 99:1659-1665 (2002).
Carnemolla et al., "Identification of a Glioblastoma-Associated Tenascin-C Isoform by a High Affinity Recombinant Antibody," American Journal of Pathology, 154(5):1345-1352 (1999).
Carnemolla et al., "Phage Antibodies with Pan-Species Recognition of the Oncofoetal Angiogenesis Marker Fibronectin ED-B Domain," International Journal of Cancer, 68:397-405 (1996).
Carsons, "Extra domain-positive fibronectins in arthritis: wolf in sheep's clothing," Rheumatology (Oxford), 40:721-723 (2001).
Castellani et al., "The Fibronectin Isoform Containing the ED-B Oncofetal Domain: A Marker of Angiogenesis," International Journal of Cancer, 59:612-618 (1994).
Castellani et al., "Transformed human cells release different fibronectin variants than do normal cells," J Cell Biol., 103:1671-1677 (1986).
Castronovo et al., "A chemical proteomics approach for the identification of accessible antigens expressed in human kidney cancer," Mol Cell Proteomics, 5:2083-2091 (2006).
Caton et al., "Identical D region sequences expressed by murine monoclonal antibodies specific for a human tumor-associated antigen," J. Immunol., 144:1965-1968 (1990).
Chadd et al., "Therapeutic antibody expression technology," Current Opinion in Biotechnology 12: 188-194 (2001).
Cheng et al., "Modification of the structure of a metallopeptide: synthesis and biological evaluation of (111)In-labeled DOTA-conjugated rhenium-cyclized alpha-MSH analogues," J. Med. Chem. 45, 3048-3056 (2002).
Chevalier et al., "Presence of ED-A Containing Fibronectin in Human Articular Cartilage from Patients with Osteoarthritis and Rheumatoid Arthritis," The Journal of Rheumatology, 23(6):1022-1030 (1996).
Chidlow et al., "Pathogenic angiogenesis in IBD and experimental colitis: new ideas and therapeutic avenues," Am J Physiol Gastrointest Liver Physiol., 293:G5-G18 (2006).
Chilosi et al., "Constitutive Expression of Tenascin in T-Dependent Zones of Human Lymphoid Tissues," American Journal of Pathology, 143(5):1348-1355 (1993).
Chothia et al., "Canonical structures for the hypervariable regions of immunoglobulins," J. Mol. Biol., 196:901-917 (1987).
Chothia et al., "Conformations of immunoglobulin hypervariable regions," Nature, 342:877-883 (1989).
Clamp et al., "The clinical potential of antiangiogenic fragments of extracellular matrix proteins," Br J Cancer, 93:967-972 (2005).
Clark et al., "Trends in antibody sequence changes during the somatic hypermutation process," Journal of Immunology, 177(1):333-340 (2006).
Claudepierre et al., "Increased Ed-B fibronectin plasma levels in spondyloarthropathies: comparison with rheumatoid arthritis patients and a healthy population," Rheumatology, 38(11):1099-1103 (1999).
Colombel et al., "Interleukin 10 (Tenovil) in the prevention of postoperative recurrence of Crohn's disease," Gut, 49:42-46 (2001).
Cseh et al., "Cell surface fibronectin on peripheral blood lymphocytes in normal individuals and in patients with acute and chronic lymphocytic leukemia and non Hodgkin's lymphoma," Allergol Immunopathol (Madr)., 13:35-40 (1985).
David et al., "A study of the structural correlates of affinity maturation: antibody affinity as a function of chemical interactions, structural plasticity and stability," Molecular Immunology, 44(6):1342-1351 (2006).
Davies et al., "Affinity improvement of single antibody VH domains: residues in all three hypervariable regions affect antigen binding," Immunotechnology, 2:169-179 (1996).

Demartis et al., "Selective targeting of tumour neovasculature by a radiohalogenated human antibody fragment specific for the ED-B domain of fibronectin," European Journal of Nuclear Medicine, 28:534-539 (2001).
Dickerson et al., "Enhancement of the antiangiogenic activity of interleukin-12 by peptide targeted delivery of the cytokine to alphavbeta3 integrin," Molecular Cancer Research, 2(12):663-673 (2004).
Doll et al., "Murine analogues of etanercept and of F8-IL10 inhibit the progression of collagen-induced arthritis in the mouse," Arthritis Res. Ther., 15:R138 (2013).
D'Ovidio et al., "Intratumoral microvessel density and expression of ED-A/ED-B sequences of fibronectin in breast carcinoma," Eur J. Cancer, 34:1081-1085 (1998).
Dr. Andrew C.R. Martin's Group, Antibody General Information V1.0 [online], Jul. 16, 1997, [retrieved on Oct. 26, 2015], Retrieved from the Internet, URL, http://www.biochem.ucl.ac.uk/_martin/abs/GeneralInfo.html.
El-Sorady et al., "Bone Marrow Angiogenesis in Patients with Hematological Malignancies: Role of VEGF," Journal of the Egyptian National Cancer Institute, 12(2):131-136 (2000).
Estey, "Modulation of angiogenesis in patients with myelodysplastic syndrome," Best Practice & Research Clinical Haematology, 17(4):623-639 (2004).
Fabbrini et al., "Selective occlusion of tumor blood vessels by targeted delivery of an antibody-photosensitizer conjugate," Int. J. Cancer, 118:1805-1813 (2006).
Fedorak et al., "Recombinant human interleukin 10 in the treatment of patients with mild to moderately active Crohn's disease. The Interleukin 10 Inflammatory Bowel Disease Cooperative Study Group," Gastroenterology, 119:1473-1482 (2000).
ffrench-Constant, "Alternative splicing of fibronectin—many different proteins but few different functions," Experimental Cell Research, 221(2):261-271 (1995).
Fiechter et al., "Comparative in vivo analysis of the atherosclerotic plaque targeting properties of eight human monoclonal antibodies," Atherosclerosis 214(2):325-330.
Franz et al., "Selective imaging of chronic cardiac rejection using a human antibody specific to the alternatively spliced Eda domain of fibronectin," 32:641-650 (2013).
Franz et al., "Targeted delivery of interleukin-10 to chronic cardiac allograft rejection using a human antibody specific to the extra domain A of fibronectin," Int J Cardiol., 195:311-322 (2015).
Fuss et al., "Both IL-12p70 and IL-23 are synthesized during active Crohn's disease and are down-regulated by treatment with anti-IL-12 p40 monoclonal antibody," Inflamm. Bowel Dis. 12:9-15 (2006).
Gafner et al., "An engineered antibody-interleukin-12 fusion protein with enhanced tumor vascular targeting properties," Int J. Cancer, 119:2205-2212 (2006).
Galeazzi et al., "A phase IB clinical trial with Dekavil (F8-IL10), an immunoregulatory 'armed antibody' for the treatment of rheumatoid arthritis, used in combination wiIh methotrexate," Isreal Medical Association Journal, 16(10):666 (2014).
Galeazzi et al., "A phase Ib clinical trial in rheumatoid arthritis of Dekavil (F8 IL10), a novel antiflammatory immunocytokine," EULAR Annual European Congress of Rheumatology, 2014, Poster SAT0232, Paris, France, Jun. 11-14, 2014.
Gerlag et al., "Suppression of murine collagen-induced arthritis by targeted apoptosis of synovial neovasculature," Arthritis Research, 3:357-361 (2001).
Giovannoni et al., "Isolation of anti-angiogenesis antibodies from a large combinatorial repertoire by colony filter screening," Nucleic Acids Research, 29(5):e27 (1-6) (2001).
Glennie et al., "Preparation and performance of bispecific F(ab' gamma)2 antibody containing thioether-linked Fab' gamma fragments," J. Immunol., 139:2367-2375.
Hahn et al., "Enhancement of the antitumor activity of interleukin-12 by targeted delivery to neovasculature," Nat Biotechnol., 20:264-269 (2002).
Hahn et al., "Tumor-targeting properties of antibody-vascular endothelial growth factor fusion proteins," Int J Cancer, 102:109-116 (2002).
Hanahan et al., "The hallmarks of cancer," Cell, 100(1):57-70 (2000).

(56) References Cited

OTHER PUBLICATIONS

Herfarth et al., "IL-10 therapy in Crohn's disease: at the crossroads. Treatment of Crohn's disease with the anti-inflammatory cytokine interleukin 10," Gut, 50:146-147 (2002).
Holliger et al., ""Diabodies": small bivalent and bispecific antibody fragments," Proc. Natl. Acad. Sci. USA, 90:6444-6448 (1993).
Holliger et al., "Engineering antibodies for the clinic," Cancer and Metastasis Rev., 18:411-419 (1999).
Holliger et al., "Engineering bispecific antibodies," Current Opinion Biotechnol., 4:446-449 (1993).
Holt et al., "Domain antibodies: proteins for therapy," Trends in Biotechnology, 21(11):484-490 (2003).
Hu et al., "Minibody: A novel engineered anti-carcinoembryonic antigen antibody fragment (single-chain Fv-CH3) which exhibits rapid, high-level targeting of xenografts," Cancer Res., 56(13):3055-3061 (1996).
Hussein et al., "Opposite expression pattern of Src kinase Lyn in acute and chronic haematological malignancies," Ann Hematol., 88:1059-1067 (2009).
Huston et al., "Protein engineering of antibody binding sites: recovery of specific activity in an anti-digoxin single-chain Fv analogue produced in *Escherichia coli*," PNAS USA, 85:5879-5883 (1988).
Jacobs et al., "Radial scars of the breast and breast carcinomas have similar alterations in expression of factors involved in vascular stroma formation," Human Pathol, 33:29-38 (2002).
Kabat et al., "Identical V region amino acid sequences and segments of sequences in antibodies of different specificities. Relative contributions of VH and VL genes, minigenes, and complementarity-determining regions to binding of antibody-combining sites," J. Immunol., 147:1709-1719 (1991).
Karp et al., "Targeting vascular endothelial growth factor for relapsed and refractory adult acute myelogenous leukemias: therapy with sequential 1-beta-d-arabinofuranosylcytosine, mitoxantrone, and bevacizumab," Clin Cancer Res., 10:3577-3585 (2004).
Kaspar et al., "Fibronectin as target for tumor therapy," International Journal of Cancer, 118:1331-1339 (2006).
Kato et al., "A new type of antimetastatic peptide derived from fibronectin," Clin Cancer Res., 8:2455-2462 (2002).
Kauma et al., "Production of Fibronectin by Peritoneal Macrophages and Concentration of Fibronectin in Peritoneal Fluid from Patients With or Without Endometriosis," Obstetrics & Gynecology, 72(1):13-18 (1988).
Knappik et al., "Fully synthetic human combinatorial antibody libraries (HuCAL) based on modular consensus frameworks and CDRs randomized with trinucleotides," J. Mol. Biol., 296:57-86 (2000).
Kohler et al., "Continuous cultures of fused cells secreting antibody of predefined specificity," Nature, 256:495-497 (1975).
Koide et al., "The fibronectin type III domain as a scaffold for novel binding proteins," Journal of Molecular Biology, 284:1141-1151 (1998).
Kornblihtt et al., "Human fibronectin: cell specific alternative mRNA splicing generates polypeptide chains differing in the number of internal repeats," Nucleic Acids Res., 12:5853-5868 (1984).
Krebs et al., "High-throughput generation and engineering of recombinant human antibodies," Journal of Immunological Methods, 254:67-84 (2001).
Kriegsmann et al., "Expression of fibronectin splice variants and oncofetal glycosylated fibronectin in the synovial membranes of patients with rheumatoid arthritis and osteoarthritis," Rheumatology International, 24:25-33 (2004).
Larrick et al., "Producing proteins in transgenic plants and animals," Current Opinion in Biotechnology, 12:411-418 (2001).
Ledermann et al., "A phase-I study of repeated therapy with radiolabelled antibody to carcinoembryonic antigen using intermittent or continuous administration of cyclosporin A to suppress the immune response," Int. J. Cancer, 47: 659-664 (1991).

Li et al., "IL-10 and its related cytokines for treatment of inflammatory bowel disease," World Journal of Gastroenterology, 10(5):620-625 (2004).
Li et al., "Mammalian cell expression of dimeric small immune proteins (SIP)," Protein Engineering, 10:731-736 (1997).
Liao et al., "The EIIIA Segment of Fibronectin Is a Ligand for Integrins a9 b1 and a4b1 Providing a Novel Mechanism for Regulating Cell Adhesion by Alternative Splicing," Journal of Biological Chemistry, 277(17):14467-14474 (2002).
Linnala et al., "Isoforms of cellular fibronectin and tenascin in amniotic fluid," FEBS Letters, 337:167-170 (1994).
Luster et al., "Plasma protein beta-2-glycoprotein 1 mediates interaction between the anti-tumor monoclonal antibody 3G4 and anionic phospholipids on endothelial cells," J Biol Chem., 281:29863-29871 (2006).
Mariani et al., "Tumor targeting potential of the monoclonal antibody BC-1 against oncofetal fibronectin in nude mice bearing human tumor implants," Cancer, 80:2378-2384 (1997).
Marlind et al., "Antibody-Mediated Delivery of Interleukin-2 to the Stroma of Breast Cancer Strongly Enhances the Potency of Chemotherapy," Clinical Cancer Research, 14(20):6515-6524 (2008).
Marlow et al., "Why interleukin-10 supplementation does not work in Crohn's disease patients," World J Gastroenterol., 19:3931-3941 (2013).
Matsumoto et al., "Expression of fibronectin isoforms in human breast tissue: production of extra domain A+/extra domain B+ by cancer cells and extra domain A+ by stromal cells," Japan J. Cancer Res., 90, 320-325 (1999).
Matter et al., "Molecular Imaging of Atherosclerotic Plaques Using a Human Antibody Against the Extra-Domain B of Fibronectin," Circulation Research, 95:1225-1233 (2004).
McCafferty et al., "Phage antibodies: filamentous phage displaying antibody variable domains," Nature, 348:552-554 (1990).
Mendez et al., "Functional transplant of megabase human immunoglobulin loci recapitulates human antibody response in mice," Nature Genet, 15:146-156 (1997).
Menrad et al., "ED-B fibronectin as a target for antibody-based cancer treatments," Expert Opin Ther Targets, 9:491-500 (2005).
Merchant et al., "An efficient route to human bispecific IgG," Nature Biotech., 16:677-681 (1998).
Moschetta et al., "Paclitaxel enhances therapeutic efficacy of the F8-IL2 immunocytokine to EDA-fibronectin-positive metastatic human melanoma xenografts," Cancer Research, 72(7):1814-1824 (2010).
Muro et al., "Regulated splicing of the fibronectin EDA exon is essential for proper skin wound healing and normal lifespan," Journal of Cell Biology, 162(1):149-160 (2003).
Neri et al., "Interfering with pH regulation in tumours as a therapeutic strategy," Nat Rev Drug Discov., 10:767-777 (2011).
Neri et al., "Tumour Vascular Targeting," Nature Review, Cancer, 5:436-446 (2005).
Niesner et al., "Quantitation of the tumor-targeting properties of antibody fragments conjugated to cell-permeating HIV-1 TAT peptides," Bioconjug Chem., 13:729-736 (2002).
Nilsson et al., "Targeted Delivery of Tissue Factor to the ED-B Domain of Fibronectin, a Marker of Angiogenesis, Mediates the Infarction of Solid Tumors in Mice," Cancer Research, 61:711-716 (2001).
Nygren et al., "Scaffolds for engineering novel binding sites in proteins," Current Opinion in Structural Biology, 7:463-469 (1997).
Okamura et al., "The Extra Domain A of Fibronectin Activates Toll-like Receptor 4," Journal of Biological Chemistry, 276(13):10229-10233 (2001).
Okayasu et al., "A novel method in the induction of reliable experimental acute and chronic ulcerative colitis in mice," Gastroenterology, 98:694-702 (1990).
Olive et al., "Endometriosis," N Engl J Med., 328:1759-1769 (1993).
Oyama et al., "Coordinate oncodevelopmental modulation of alternative splicing of fibronectin pre-messenger RNA at ED-A, ED-B, and CS1 regions in human liver tumors," Cancer Res., 53:2005-2011 (1993).

(56) References Cited

OTHER PUBLICATIONS

Oyama et al., "Deregulation of Alternative Splicing of Fibronectin Pre-mRNA in Malignant Human Liver Tumors," Journal of Biological Chemistry, 264(18:10331-10334 (1989).
Oyama et al., "Oncodevelopmental Regulation of the Alternative Splicing of Fibronectin Pre-Messenger RNA in Human Lung Tissues," Cancer Research, 50(4):1075-1078 (1990).
Padlan, "Anatomy of the antibody molecule," Mol Immunol., 31:169-217 (1994).
Padro et al., "Increased angiogenesis in the bone marrow of patients with acute myeloid leukemia," Blood, 95(8):2637-2644 (2000).
Padro et al., "Overexpression of vascular endothelial growth factor (VEGF) and its cellular receptor KDR (VEGFR-2) in the bone marrow of patients with acute myeloid leukemia," Leukemia., 16:1302-1310 (2002).
Paganelli et al., "Pre-targeted immunodetection in glioma patients: tumour localization and single-photon emission tomography imaging of 99mTc]PnAObiotin," European Journal of Nuclear Medicine, 21:314-321 (1994).
Paolella et al., "Sequence analysis and in vivo expression show that alternative splicing of ED-B and ED-A regions of the human fibronectin gene are independent events," Nucleic Acids Res., 16:3545-3557 (1988).
Pasche et al, "Immunocytokines: a novel class of potent armed antibodies," Drug Discov Today, 17 (11-12):583-590 (2012).
Pasche et al., "Cloning and characterization of novel tumor-targeting immunocytokines based on murine IL7," J Biotechnol., 154:84-92 (2011).
Pasche et al., "The antibody-based delivery of interleukin-12 to the tumor neovasculature eradicates murine models of cancer in combination with paclitaxel," Clin Cancer Res., 18:4092-4103 (2012).
Paul, Fundamental Immunogy, 3rd Edition, pp. 292-295 (1993).
Payne, "Progress in immunoconjugate cancer therapeutics," Cance Cell, 3:207-212 (2003).
Peters et al., "Preferential Recognition of a Fragment Species of Osteoarthritic Synovial Fluid Fibronectin by Antibodies to the Alternatively Spliced EIIIA Segment," Arthritis and Rheumatism, 44(11):2572-2585 (2001).
Reiter et al., "Engineering antibody Fv fragments for cancer detection and therapy: disulfide-stabilized Fv fragments," Nature Biotech, 14:1239-1245 (1996).
Ridgeway et al., "'Knobs-into-holes' engineering of antibody CH3 domains for heavy chain heterodimerization," Protein Eng., 9:616-621 (1996).
Riva et al., "Local Treatment of Malignant Gliomas by Direct Infusion of Specific Monoclonal Antibodies Labeled with 131 I: Comparison of the Results Obtained in Recurrent and Newly Diagnosed Tumors," Cancer Research, 55:5952s-5956s (1995).
Riva et al., "Treatment of Intracranial Human Glioblastoma by Direct Intratumoral Administration of 131I-Labelled Anti-Tenascin Monoclonal Antibody BC-2," International Journal of Cancer, 51:7-13 (1992).
Rodig et al., "Heterogeneous CD52 expression among hematologic neoplasms: implications for the use of alemtuzumab (CAMPATH-1H)," Clin Cancer Res., 2:7174-7179 (2006).
Rudikoff et al., "Single amino acid substitution altering antigen-binding specificity," PNAS, 79(6):1979-1983 (1982).
Rybak et al., "Ligand-Based Vascular Targeting of Disease," ChemMedChem, 2:22-40 (2007).
Rybak et al., "The Extra-domain A of Fibronectin Is a Vascular Marker of Solid Tumors and Metastases," Cancer Research, 67(22):10948-10957 (2007).
Santimaria et al., "Immunoscintigraphic detection of the ED-B domain of fibronectin, a marker of angiogenesis, in patients with cancer," Clin Cancer Res., 9:571-579 (2003).
Scarpino et al., "Expression of EDA/EDB Isoborms of Fibronectin in Papillary CarcinomaoftheThyroid," Journal of Pathology, 188:163-167 (1999).

Schliemann et al., "Complete eradication of human B-cell-lymphoma xenografts using rituximab in combination with the immunocytokine L19-IL2," Blood, 113:2275-2283 (2009).
Schliemann et al., "Three clinical-stage tumor targeting antibodies reveal differential expression of oncofetal fibronectin and tenascin-C isoforms in human ymphoma," Leukemia Research, 33:1718-1722 (2009).
Schrama et al., "Antibody targeted drugs as cancer therapeutics," Nature Reviews, Drug Discovery, 5:147-159 (2006).
Schreiber et al., "Safety and efficacy of recombinant human interleukin 10 in chronic active Crohn's disease. Crohn's Disease IL-10 Cooperative Study Group," Gastroenterology, 119:1461-1472 (2000).
Schwager et al., "A comparative immunofluorescence analysis of three clinical-stage antibodies in head and neck cancer, " Head & Neck Oncology, 3:25 (2011).
Schwager et al., "Preclinical characterization of DEKAVIL (F8-IL10), a novel clinical-stage immunocytokine which inhibits the progression of collagen-induced arthritis," Arthritis Research Therapy, 11(5):R142 (15 pages) (2009).
Schwager et al., "The antibody-mediated targeted delivery of interleukin-10 inhibits endometriosis in a syngeneic mouse model," Hum. Reprod. 26(9) 2344-2352 (2011).
Segal et al., "The three-dimensional structure of a phosphorylcholine-binding mouse immunoglobulin Fab and the nature of the antigen binding site," PNAS USA, 71:4298-4302 (1974).
Sharon et al., "Structural characterization of idiotopes by using antibody variants generated by site-directed mutagenesis," J. Immunol., 144:4863-4869 (1990).
Sharon et al., "Structural correlates of high antibody affinity: three engineered amino acid substitutions can increase the affinity of an anti-p-azophenylarsonate antibody 200-fold," PNAS USA, 87:4814-4817 (1990).
Shibata et al.. "Immunoregulatory roles of IL-10 in innate immunity: IL-10 inhibits macrophage production of IFN-gamma-inducing factors but enhances NK cell production of IFN-gamma," J Immunol., 161:4283-4288 (1998).
Shiozawa et al., "Alternatively spliced EDA-containing fibronectin in synovial fluid as a predictor of rheumatoid joint destruction," Rheumatology, 40(7):739-742 (2001).
Silacci et al., "Human monoclonal antibodies to domain C of tenascin-C selectively target solid tumors in vivo," Protein Eng Des Sel., 19:471-478 (2006).
Smith et al., "Computerized analysis of tumor cell interactions with extracellular matrix proteins, peptides, and endothelial cells under laminar flow," Biotechnol Bioeng., 50:598-607 (1996).
Smolej et al., "Choice of endothelial marker is crucial for assessment of bone marrow microvessel density in chronic lymphocytic leukemia," APMIS, 116 (12):1058-1062 (2008).
Soini et al., "Tenascin immunoreactivity in normal and pathological bone marrow," Journal of Clinical Pathology, vol. 46(3):218-221 (1993).
Sommavilla et al., "Expression, engineering and characterization of the tumor-targeting heterodimeric immunocytokine F8-IL12," Protein Eng Des Sel., 23:653-661 (2010).
Spaeth et al., "Radioimmunothempy targeting the extra domain B of fibronectin in C6 rat gliomas: a preliminary study about the therapeutic efficacy of iodine-131-labeled SIP(L19)," Nucl Med Biol., 33:661-666 (2006).
Staerz et al., "Hybrid hybridoma producing a bispecific monoclonal antibody that can focus effector T-cell activity," PNAS USA, 83:1453-1457 (1986).
Strober et al., "The fundamental basis of inflammatory bowel disease," The Journal of Clinical Investigation, 117(3), 514-521 (2007).
Summers et al., "Trichuris suis seems to be safe and possibly effective in the treatment of inflammatory bowel disease," Am. J. Gastroentol., 98:2034-2041(2003).
Suresh et al., "Bispecific monoclonal antibodies from hybrid hybridomas," Method. Enzymol., 121:210-228 (1986).
Tagashira et al., "Interleukin-10 attenuates TNF-alpha-induced interleukin-6 production in endometriotic stromal cells," Fertil Steril., 91:2185-2192 (2009).

(56) References Cited

OTHER PUBLICATIONS

Tamura et al., "Structural correlates of an anticarcinoma antibody: identification of specificity-determining residues (SDRs) and development of a minimally immunogenic antibody variant by retention of SDRs only," J. Immunol., 164:1432-1441 (2000).
Tarli et al., "A High-Affinity Human Antibody That Targets Tumoral Blood Vessels," Blood, 94(1):192-198 (1999).
Tavian et al., "RT-PCR detection of fibronectin EDA+ and EDB+ mRNA isoforms: molecular markers for hepatocellular carcinoma," Int. J. Cancer, 56:820-825 (1994).
Taylor et al., "VEGF and imaging of vessels in rheumatoid arthritis," Arthritis Research, 4(3):599-5107 (2002).
Thrope, "Vascular Targeting Agents as Cancer Therapeutics," Clinical Cancer Research, 10:415-427 (2004).
Tijink et al., "Radioimmunotherapy of head and neck cancer xenografts using 131I-labeled antibody L19-SIP for selective targeting of tumor vasculature," J Nucl Med., 47:1127-1135 (2006).
Tilg et al., "Treatment of Crohn's disease with recombinant human interleukin 10 induces the proinflammatory cytokine interferon gamma," Gut, 50:191-195 (2002).
Trachsel et al., "A Human mAb Specific to Oncofetal Fibronectin Selectively Targets Chronic Skin Inflammation in vivo," Journal of Investigative Dermatology, 127:881-886 (2007).
Trachsel et al., "Antibodies for angiogenesis inhibition, vascular targeting and endothelial cell transcytosis," Advanced Drug Delivery Reviews, 58:735-754 (2007).
Trachsel et al., "Antibody-mediated delivery of IL-10 inhibits the progression of established collagen-induced arthritis," Arthritis Research and Therapy, 9(1):R9 (2007).
Vajdos et al., "Comprehensive functional maps of the antigen-binding site of an anti-ErbB2 antibody obtained with shotgun scanning mutagenesis," Journal of Molecular Biology, 320(2):415-428 (2002).
van de Loo et al, "Immunocytokines: the long awaited therapeutic magic bullet in rheumatoid arthritis?" Arthritis Res. Ther. 11(6):132 (2009).
Varito et al., "Differential expression of the ED sequence-containing form of cellular fibronectin in embryonic and adult human tissues," Journal of Cell Science, 88:419-430 (1987).
Varma et al., "Endometriosis and the neoplastic process," Reproduction, 127:293-304 (2004).
Villa et al., "A high-affinity human monoclonal antibody specific to the alternatively spliced EDA domain of fibronectin efficiently targets tumor neovasculature in vivo," International Journal of Cancer, 122:2405-2413 (2008).
Viti et al., "Increased Binding Affinity and Valence of Recombinant Antibody Fragments Lead to Improved Targeting of Tumoral Angiogenesis," Cancer Research, 59:347-352 (1999).
Wallace et al., "Media hype and drug discovery," Drug Discovery Today 3:433-434 (1998).
Walsh et al., "Focally Regulated Endothelial Proliferation and Cell Death in Human Synovium," American Journal of Pathology, 152(3):691-702 (1998).
Wang et al. "Identification of a Mutated Fibronectin as a Tumor Antigen Recognized by CD4+ T Cells: Its Role in Extracellular Matrix Formation and Tumor Metastasis," The Journal of Experimental Medicine, 195(11):1397-1406 (2002).
Ward et al., "Binding activities of a repertoire of single immunoglobulin variable domains secreted from *Escherichia coli*," Nature, 341:544-546 (1989).
Wieckowski et al., "Therapeutic efficacy of the F8-IL2 immunocytokine in a metastatic mouse model of lung adenocarcinoma," Lung Cancer, 88(10:9-15 (2015).
Zalutsky et al., "A method for the radiohalogenation of proteins resulting in decreased thyroid uptake of radioiodine," Appl. Radiat. Isot., 38:1051-1055 (1987).
Zalutsky et al., "Radiohalogenation of a monoclonal antibody using an N-succinimidyl 3-(tri-n-butylstannyl)benzoate intermediate," Cancer Research, 48:1446-1450 (1988).
Zardi et al., "Transformed human cells produce a new fibronectin isoform by preferential alternative splicing of a previously unobserved exon," EMBO J., 6:2337-2342 (1987).
Sun et al., "Analysis of Intestinal Fibrosis in Chronic Colitis in Mice Induced by Dextran Sulfate Sodium," Gastroenterology, 140(5, Suppl. 1):p. S-520 Su1961 (2011) (1 page).
Suzuki et al., "Analysis of intestinal fibrosis in chronic colitis in mice induced by dextran sulfate sodium," Pathology International, 61(4):228-238 (2011).
Yamaguchi et al., "Irsogladine maleate ameliorates inflammation and fibrosis in mice with chronic colitis induced by dextran sulfate sodium," Medical Molecular Morphology, 45(3):140-151 (2012).

* cited by examiner

Figure 1A

EVQLLESGGGLVQPGGSLRLSCAASGFTFSLFTMSWVRQAPGKGLEWVSAISGSGGSTYYAD
SVKGRFTISRDNSKNTLYLQMNSLRAEDTAVYYCAKSTHLYLFDYWGQGTLVTVSS (SEQ ID NO: 7)

Figure 1B

GGSGG (SEQ ID NO: 9)

Figure 1C

EIVLTQSPGTLSLSPGERATLSCRASQSVSMPELAWYQQKPGQAPRLLIYGASSRATGIPDRFSG
SGSGTDFTLTISRLEPEDFAVYYCQQMRGRFPTFGQGTKVEIK (SEQ ID NO: 8)

Figure 1D

SSSSGSSSSGSSSSG (SEQ ID NO: 10)

Figure 1E

SPQQQTQSENSCTHFPGNLPNMLRDLRDAFSRVKTFFQMKDQLDNLLLKESLLEDFKGYLGC
QALSEMIQFYLEEVMPQAENQDPDIKAHVNSLGENLKTLRLRLRRCHRFLPCENKSKAVEQV
KNAFNKLQEKGIYKAMSEFDIFINYIEAYMTMKIRN (SEQ ID NO: 11)

Fig. 4A
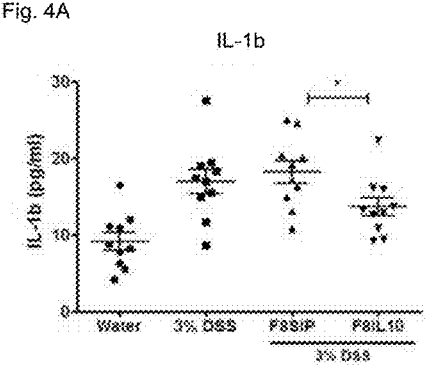
Fig. 4B
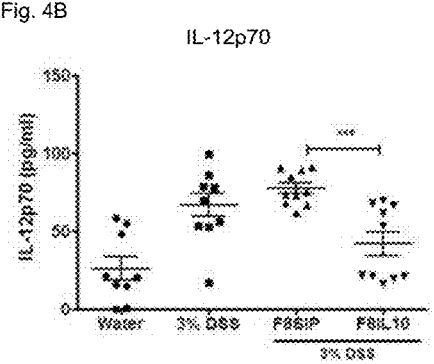
Fig. 4C
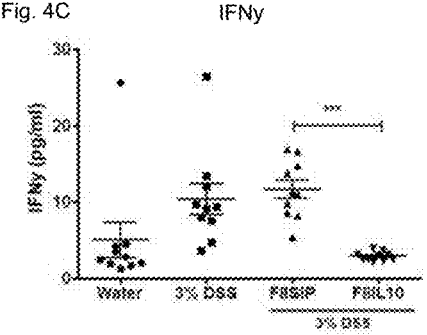
Fig. 4D
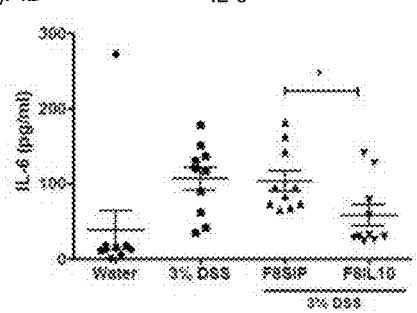
FIGURE 4

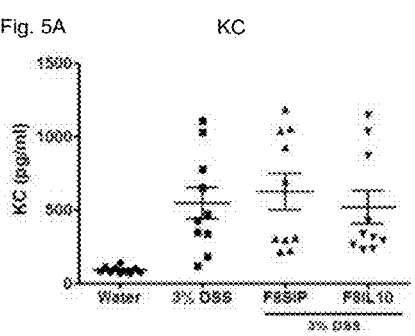
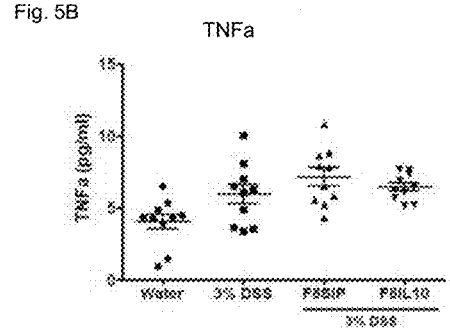
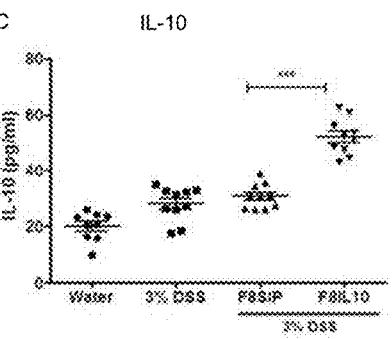
FIGURE 5

Fig. 6A
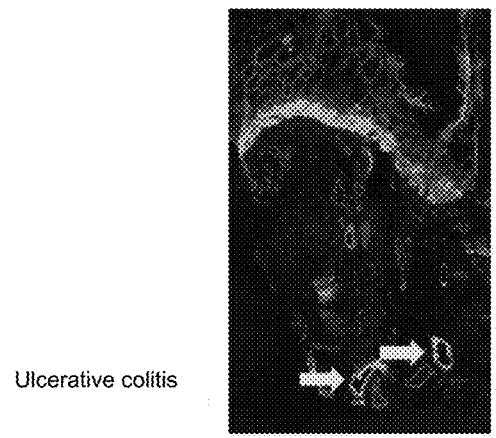
Ulcerative colitis
Fig. 6B
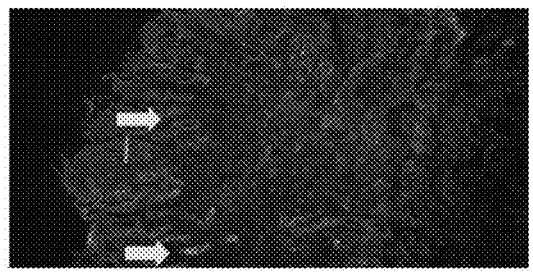
Crohn's disease
Figure 6

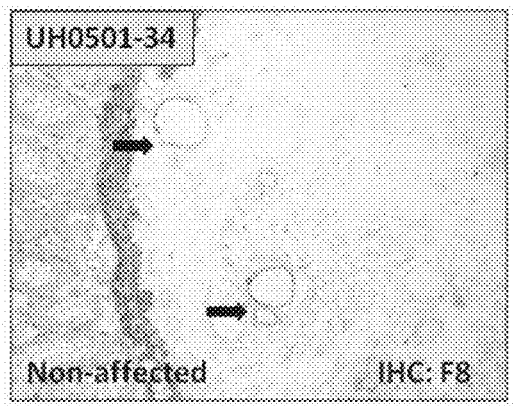
Fig. 7A
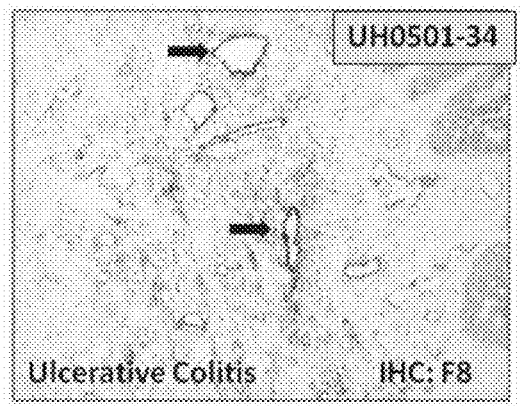
Fig. 7B
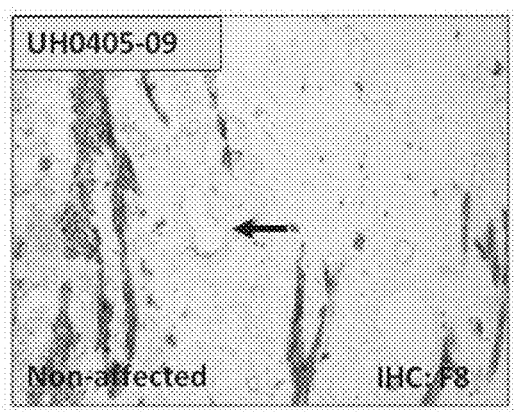
Fig. 7C
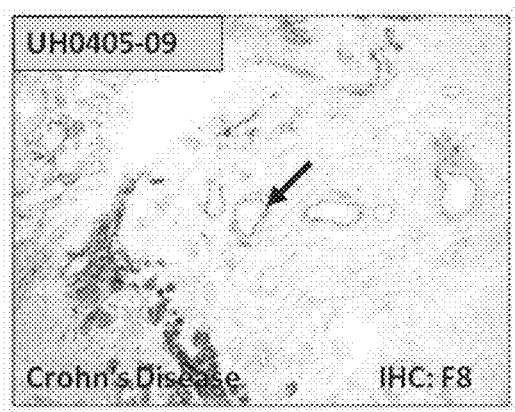
Fig. 7D
Figure 7

ANTI-ED-A IMMUNOCONJUGATES FOR INFLAMMATORY BOWEL DISEASE

CROSS-REFERENCE TO RELATED APPLICATIONS

This application is a continuation of U.S. patent application Ser. No. 14/431,745, filed Mar. 26, 2015, (allowed) which is the § 371 U.S. National Stage of International Application No. PCT/US2012/058574, filed Oct. 3, 2012, (expired) which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 1, 2017, is named PCFC-684-302-SL.Txt and is 10,525 bytes in size.

The present invention relates to the treatment and detection of inflammatory bowel disease (IBD). The invention involves use of a specific binding member that binds the ED-A isoform of fibronectin, especially a specific binding member that binds domain ED-A of fibronectin. The specific binding member may, for example, be conjugated to an immunosuppressive or anti-inflammatory molecule, such as interleukin-10.

BACKGROUND TO THE INVENTION

Inflammatory Bowel Disease (IBD) is a group of inflammatory conditions that affect colon and small intestine. The major types of IBD are Crohn's disease (CD) and ulcerative colitis (UC). IBD pathogenesis is characterized by different angiogenic regulation contributing to and perpetuating a chronic inflammatory state in the bowel (Chidlow et al., 2006, Am J Physiol. Gastrointest. Liver Physiol., 29, G5-G18). Crohn's disease can affect any part of the gastrointestinal tract, whereas ulcerative colitis is typically restricted to the colon and rectum (Summers R W, Elliott D E, Qadir K, Urban J F, Thompson R, Weinstock J V (2003) Am. J. Gastroentol., 98:2034-2041). Depending on its severity, treatment of ulcerative colitis may requite immunosuppression to control its symptoms and treatment usually involves the administration of anti-inflammatory molecules.

IBD is known to be characterized by upregulation of pro-inflammatory cytokines, such as IFN-γ, IL-6 and IL-12 (e.g. IL-12p70). For example, Crohn's disease is known to be associated with excess IL-12/IL-23 and IFN-γ/IL-17 production (Strober et al. (2007), The Journal of Clinical Investigation, 117(3), 514-521). Synthesis of IL-12p70 and IL-23 during active Chron's disease has also been reported (Fuss et. al. 2006, Inflamm. Bowel Dis. 12:9-15).

Fibronectin (FN) is a glycoprotein and is widely expressed in a variety of normal tissues and body fluids. It is a component of the extracellular matrix (ECM), and plays a role in many biological processes, including cellular adhesion, cellular migration, haemostasis, thrombosis, wound healing, tissue differentiation and oncogenic transformation.

Different FN isoforms are generated by alternative splicing of three regions (ED-A, ED-B, IIICS) of the primary transcript FN pre-mRNA, a process that is modulated by cytokines and extracellular pH (Balza (1988) FEBS Lett., 228, 42-44; Carnemolla (1989) J. Cell Biol., 106, 1139-1148; Borsi (1990) FEBS Lett. 261, 175-178). Fibronectin contains two type-III globular extra-domains which may undergo alternative splicing; ED-A and ED-B (ffrench-Constant (1955) Exp. Cell Res., 22, 261-271, Kasper et al. (2006) Int. J. cancer, 118, 1331-1339). The ED-As of mouse fibronectin and human fibronectin are 96.7% identical (only 3 amino acids differ between the two 90 amino acid sequences).

Expression of the ED-A of fibronectin has been reported in tumour cells and in solid tumours at the mRNA level in breast cancer (Jacobs et al. (2002) Human Pathol, 33, 29-38, Matsumoto et al. (1999) Jpn. J. Cancer Res., 90, 320-325) and liver cancer (Oyama et al. (1989) JBC, 264, 10331-10334, Tavian et al. (1994) Int. J. Cancer, 56, 820-825) and at the level of isolated protein in fibrosarcoma, rhabdomyosarcoma and melanoma (Borsi et al. (1987) J. Cell Biol., 104, 595-560). Other than cancer, expression of the ED-A of fibronectin has been reported in rheumatoid arthritis (WO2009/056268). WO2010/078950 also reports expression of ED-A of fibronectin in endometriosis, psoriasis and psoriatic arthritis, however histochemical analysis revealed a very weak to virtually absent expression of ED-A in multiple sclerosis and in ulcerative colitis. Immunohistochemical analyses reported by Brenmoehl et al. (Int. J. Colorectal Dis. (2007) 22:611-623) show that ED-A expression is decreased in inflamed intestinal mucosa of CD patients when compared to control mucosa and increased in ulcerative colitis. Brenmoehl et al. (2007) also report increased expression of ED-A and ED-B isoforms in fibrotic mucosa of CD patients. Expression of ED-A and ED-B isoforms in fibrotic mucosa is expected as these fibronectin isoforms are known to be involved in wound healing. There is no suggestion in Brenmoehl et al. (2007) that ED-A is expressed during (active) CD, given the decreased expression of ED-A in inflamed intestinal mucosa of CD patients compared with mucosa derived from control patients. The use of binding members which bind the ED-A isoform of fibronectin for the treatment or diagnosis of IBD is also not disclosed in this document.

Interleukin-10 (IL-10) is an anti-inflammatory cytokine that functions as an important regulator of immune system. Although IL-10 is known to have many different roles in the immune system, its two major activities include inhibition of cytokine production by macrophages and inhibition of the accessory functions of macrophages during T cell activation (Abbas A, Lichtman A, Pober J., 1994, Cellular and Molecular Immunology. 2nd Ed. Philadelphia: W.B. Saunders Company). The effects of these actions cause IL-10 to play mainly an anti-inflammatory role in the immune system. IL-10 was originally known as the cytokine synthesis inhibiting factor (CSIF), and the discovery of this protein was based on its biological activity (Delves P, Roitt I (eds), 1998, Encyclopedia of Immunology, 2nd Ed. San Diego: Academic Press). Because of its well known anti-inflammatory properties, IL-10 therapy was introduced as a potential new anti-inflammatory therapy in Chron's disease (CD) (Fedorak et al., Gastroenterology (2000) 119, 1473-1482; Schreiber et al., Gastroenterology (200) 119, 1461-1472; Colombel et al., Gut (2001) 49, 41-46).

Asadullah et al. (Pharmacology Reviews, (2003), 55, 245-269) review the state of the art of Interleukin-10 therapy in a number of inflammatory diseases. When reviewing chronic inflammatory bowel disease, Asadullah et al. report that several large multicenter trials were performed, testing multiple IL-10 dosages in patients with mild/moderate or therapy refractory CD, as well as in patients undergoing curative ileal or ileocolonic resection to prevent endoscopic postoperative occurrence by systemic administration (Fedorak et al., Gastroenterology) (2000) 119, 1473-1482; Schreiber et al., Gastroenterology (2000) 119, 1461-1472; Colombel et al., Gut (2001) 49, 42-46.). The data indicate that IL-10 therapy is safe and well tolerated. However, IL-10 treatment did not result in significantly higher remission rates or clinical improvement compared with placebo treatment.

Overall the clinical results were found to be unsatisfying and several explanations for the disappointment with this therapeutic strategy were discussed by Herfarth and Scholmerich (Gut (2002) 50, 146-147).

Therefore, there is a need for effective treatments of various IBD states.

STATEMENT OF INVENTION

The present inventors have surprisingly found that, an anti-EDA antibody fused to IL-10, was able (i) to localise selectively at sites of inflamed colon in vivo in IBD diseased mice and (ii) to decrease the serum levels of certain pro-inflammatory cytokines in the IBD diseased mice, in particular interferon-gamma, IL-6 and IL-12p70.

Downregulation of pro-inflammatory cytokines through administration of an anti-EDA antibody fused to IL-10 was particularly surprising as Tilg et al. (Gut (2002), 50, 191-195) report that treatment of Crohn's disease patients with recombinant human IL-10 induces interferon-gamma. Shibata et al. (J. Immunol., (1998) 161, 4283-4288) also report that IL-10 enhances NK cell production of INF-gamma but inhibits macrophage production of IFN-gamma-inducing factors.

Therefore, in a first aspect, the invention provides a specific binding member, e.g. an antibody molecule, that binds the Extra Domain-A (ED-A) isoform of fibronectin (A-FN) for use in a method of treatment of IBD. The invention also provides the use of a specific binding member, e.g. an antibody molecule, that binds the Extra Domain-A (ED-A) isoform of fibronectin for the manufacture of a medicament for treating IBD. The invention also provides a method of treating EBD in a patient, the method comprising administering to a patient a therapeutically effective amount of a medicament comprising a specific binding member which binds the ED-A isoform of fibronectin. Preferably, the specific binding member binds the ED-A isoform of human fibronectin.

The specific binding member, e.g. an antibody molecule, for use in this first aspect of the invention, may bind the ED-A of fibronectin.

The specific binding member e.g. an antibody molecule, for use in this first aspect of the invention, may be conjugated to a molecule that has immunosuppressive or anti-inflammatory activity, a detectable label, a radioisotope, or a bioactive molecule, such as a cytokine, a hormone, a therapeutic radioisotope, a cytotoxic drug. The specific binding member may be conjugated to the bioactive molecule by a cleavable linker.

In a preferred embodiment, the specific binding member, e.g. antibody molecule, is conjugated to a molecule that has immunosuppressive or anti-inflammatory activity, such as IL-10.

IBD, as referred to herein, may active IBD. In particular, the IBD may be Crohn's disease (CD), ulcerative colitis (UC), collagenous colitis, lymphocytic colitis, ischaemic colitis, diversion colitis, Behçet's disease or indeterminate colitis. The IBD may be CD or UC. The IBD may be CD, collagenous colitis, lymphocytic colitis, ischaemic colitis, diversion colitis, Behçet's disease or indeterminate colitis.

In one embodiment, the IBD is not UC. The IBD may be an IBD which is not typically restricted to inflammation in the colon and the rectum, such as CD. The IBD may be an IBD which does not affect only the lining of the colon. Preferably, the IBD in CD. The terms CD, UC, collagenous colitis, lymphocytic colitis, ischaemic colitis, diversion colitis, Behçet's disease and indeterminate colitis, as used herein, may refer to active CD, active UC, active collagenous colitis, active lymphocytic colitis, active ischaemic colitis, active diversion colitis, active Behçet's disease and active indeterminate colitis, respectively.

In a second aspect, the invention provides a specific binding member, e.g. an antibody molecule, that binds the ED-A isoform of fibronectin for use in the delivery to IBD tissue of a molecule conjugated to the specific binding member. The invention also provides the use of a specific binding member, e.g. an antibody molecule, chat binds the ED-A isoform of fibronectin for the manufacture of a medicament for delivery to IBD tissue of a molecule conjugated to the specific binding member. The invention also provides a method of delivering a molecule to IBD tissue in a human or animal, wherein the molecule is conjugated to a specific binding member which binds the ED-A isoform of fibronectin to form a conjugate and the method comprises administering the conjugate to the human or animal. Preferably, the specific binding member binds the ED-A isoform of human fibronectin.

The specific binding member e.g. an antibody molecule, for use in this second aspect of the invention, may bind the ED-A of fibronectin.

The specific binding member e.g. an antibody molecule, for use in this second aspect of the invention, may be conjugated to a detectable label, a radioisotope, or a bioactive molecule, such as a cytokine, a hormone, a therapeutic radioisotope or a cytotoxic drug. The specific binding member may be conjugated to the bioactive molecule by a cleavable linker.

The specific binding member, e.g. antibody molecule, is preferably conjugated to IL-10.

In a third aspect, the invention provides a specific binding member, e.g. an antibody molecule, that binds the ED-A isoform of fibronectin for use in a method of diagnosis of IBD. The invention also provides use of a specific binding member that binds the ED-A isoform of fibronectin for the manufacture of a diagnostic product for diagnosing IBD. The invention also provides a method of detecting or diagnosing IBD in a human or animal, wherein the method comprises the steps of:
  (a) administering to the human or animal a specific binding member which binds the ED-A domain of fibronectin, and
  b) determining the presence on absence of the specific binding member in sites of IBD of the human or animal body,
    wherein localisation of the specific binding member to site of IBD indicates the presence of IBD.

Preferably, the specific binding member binds the ED-A isoform of human fibronectin.

The specific binding member, e.g. an antibody molecule, for use in this third aspect of the invention, may bind the ED-A of fibronectin.

The specific binding member e.g. an antibody molecule, for use in this third aspect of the invention, may be conjugated to a detectable label, or a radioisotope.

In a fourth aspect, the invention provides a specific binding member that binds the ED-A isoform of fibronectin for use in a method of imaging IBD tissue. The invention also provides use of a specific binding member that binds the ED-A isoform of fibronectin for the manufacture of an imaging agent for imaging IBD tissue. The invention also provides a method of detecting or imaging IBD tissue in a human or animal, wherein the method comprises the steps of:

(a) administering to the human or animal a specific binding member which binds the ED-A domain of fibronectin, and (b) detecting the binding of the specific binding member to IBD tissue in the human or animal body.

Preferably, the specific binding member binds the ED-A isoform of human fibronectin.

The specific binding member, e.g. so antibody molecule, for use in this fourth aspect of the invention, may bind the ED-A of fibronectin.

The specific binding member e.g. an antibody molecule, for use in this fourth aspect of the invention, may be conjugated to a detectable label, or a radioisotope.

In a fifth aspect, the invention provides a conjugate comprising a binding member which binds the ED-A isoform, e.g. the ED-A, of fibronectin conjugated to IL-10, wherein the conjugate has the sequence shown in SEQ ID NO: 13. This conjugate is referred to as F8-IL10 herein. As the VH and VL domains of this conjugate are linked by means of a 5 amino acid linker (see FIG. 1B), the conjugate is expected to form noncovalent homodimers in solution.

A specific binding member for use in the invention may be an antibody molecule which binds the ED-A isoform of fibronectin and/or the ED-A of fibronectin, wherein the antibody comprises one or more complementarity determining regions (CDRs) of the F8 antibody described herein. These sequences are provided below (see SEQ ID NOs: 1-6). The CDR sequences of the F8 antibody are also shown in FIG. 1.

A specific binding member for use in the invention may comprise one or more CDRs as described herein, e.g. a CDR3, and optionally also a CDR1 and CDR2 to form a set of CDRs.

Preferably, a specific binding member for use in the invention comprises a set of H and/or L CDRs of antibody the F8 antibody described herein with ten or fewer, e.g. one, two, three, four, or five, amino acid substitutions within the disclosed set of H and/or L CDRs.

Substitutions may potentially be made at any residue within the set of CDRs, and may be within CDR1, CDR2 and/or CDR3.

A specific binding member for use in the invention may comprise an antibody molecule, e.g. a human antibody molecule. The specific binding member normally comprises an antibody VH and/or VL domain. VH domains of specific binding members are also provided for use in the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. All VH and VL sequences, CDR sequences, sets of CDRs and sets of HCDRs and sets of LCDRs disclosed herein represent embodiments of a specific binding member for use in the invention. As described herein, a "set of CDRs" comprises CDR1, CDR2 and CDR3. Thus, a set of HCDRs refers to HCDR1, HCDR2 and HCDR3, and a set of LCDRs. refers to LCDR1, LCDR2 and LCDR3. Unless otherwise stated, a "set of CDRs" includes HCDRs and LCDRs.

A specific binding member for use in the invention may comprise an antibody VH domain comprising complementarity determining regions HCDR1, HCDR2 and HCDR3 and a framework, wherein HCDR1 is SEQ ID NO: 1, and wherein optionally HCDR2 is SEQ ID NO: 2, and/or HCDR3 is SEQ ID NO: 3.

Typically, a VH domain is paired with a VL domain to provide an antibody antigen-binding site, although as discussed further below, a VH or VL domain alone may be used to bind antigen. Thus, a specific binding member for use in the invention may further comprise an antibody VL domain comprising complementarity determining regions LCDR1, LCDR2 and LCDR3 and a framework, wherein LCDR1 in SEQ ID NO: 4, and wherein optionally LCDR2 is SEQ. ID NO: 5 and/or LCDR3 is SEQ ID NO: 6.

A specific binding member for use in the invention may preferably comprise an antibody molecule for the ED-A of fibronectin, wherein the antibody molecule comprises a VH domain and a VL domain, wherein the VH domain comprises a framework and a set of complementarity determining regions HCDR1, HCDR2 and HCDR3 and wherein the VL domain comprises complementarity determining regions LCDR1, LCDR2 and LCDR3 and a framework, and wherein
HCDR1 has amino acid sequence SEQ ID NO: 1;
HCDR2 has amino acid sequence SEQ ID NO: 2;
HCDR3 has amino acid sequence SEQ ID NO: 3;
LCDR1 has amino acid sequence SEQ. ID NO: 4;
LCDR2 has amino acid sequences SEQ ID NO: 5; and
LCDR3 has amino acid sequence SEQ ID NO: 6.

One or more CDRs or a set of CDRs of an antibody may be grafted into a framework (e.g. human framework) to provide an antibody molecule for use in the invention. Framework regions may comprise human germline gene segment sequences. Thus, the framework may be germlined, whereby one or more residues within the framework are changed to match the residues at the equivalent position in the most similar human germline framework. A specific binding member for use in the invention may be an isolated antibody molecule having a VH domain comprising a set of HCDRs in a human germline framework, e.g. DP47. Normally the specific binding member also has a VL domain comprising a set of LCDRs, e.g. in a human germline framework. The human germline framework of the VL domain may be DPK22.

A VH domain for use in the invention may preferably have amino acid sequence SEQ ID NO: 7, which is the VH domain of the F8 antibody. A VL domain for use in the invention may preferably have amino acid sequence SEQ ID NO: 8, which is the VL domain of the wildtype F8 antibody.

A specific binding member for use in the invention may be or comprise a single chain Fv (scFv), comprising a VH domain and a VL domain joined via a peptide linker. The skilled person may select an appropriate length and sequence of linker, e.g. at least 5 or at least 10 amino acids in length, up to about 15, up to about 20 or up to about 25 amino acids in length. The linker may have the amino acid sequence GGSGG (SEQ ID NO: 9).

The specific binding member may be a diabody, which is a multivalent or multispecific fragment constructed by gene fusion (WO94/13804; Holliger et al. (1993a), Proc. Natl. Acad. Sci. USA 90 6444-6448).

Preferably, the specific binding member is a scFv which forms (stable) noncovalent homodimers in solution. For example, the F8 antibody and F8-IL10 conjugate described herein both comprise an scFv which is expected to form (stable) noncovalent homodimers in solution.

A single brain Fv (scFv) may be comprised within a mini-immunoglobulin or small immunoprotein (SIP), e.g. as described in (Li et al., (1997), Protein Engineering, 10: 731-736). An SIP may comprise an scFv molecule fused to the CH4 domain of the human IgE secretory isoform IgE-S2 ($\epsilon_{S2}$-CH4; Batista et al., (1996), J. Exp. Med., 184: 2197-205) forming an homo-dimeric mini-immunoglobulin antibody molecule.

Alternatively, a specific binding member for use in the invention may comprise an antigen-binding site within a non-antibody molecule, normally provided by one or more CDRs e.g. a set of CDRs in a non-antibody protein scaffold. Specific binding members, including non-antibody and antibody molecules, are described in more detail elsewhere herein.

The specific binding member for use in the present invention may be an antibody molecule comprising the VH domain of the F8 antibody shown in SEQ ID NO: 7 and/or the VL domain of the F8 antibody shown in SEQ ID NO: 8. The specific binding member for use in the present invention may be an antibody molecule comprising the sequence shown in SEQ ID NO: 11. The specific binding member conjugated to IL-10 of the present invention may comprise the sequence shown in SEQ ID NO: 13.

A specific binding member for use in the present invention may also comprise one or more, for example all six, of the CDRs of anti ED-A antibodies H1, B2, C5, D5, E5, C8, F1, B7, E8 or G9 or variants thereof, or the VH and/or VL domains of anti ED-A antibodies H1, B2, C5, D5, E5, C8, F1, B7, E8 or G9 or variants thereof. The CDR sequences and VH and VL domain sequences of these antibodies are disclosed in WO2010/078950.

A suitable variant for use in the present invention comprises an antibody antigen binding site comprising a VH domain and a VL domain of the F8 antibody described herein, wherein the leucine (L) residue at position 5 of the VH domain shown as SEQ ID NO: 7 is substituted with valine (V) and/or the arginine (R) residue at position 18 of the VL domain shown as SEQ ID NO: 8 is substituted with lysine (K).

These and other aspects of the invention are described in further detail below.

BRIEF DESCRIPTION OF THE FIGURES

FIG. 1A shows the amino acid sequence of the anti-ED-A F8 antibody heavy chain (VH) (SEQ ID NO: 7). The amino acid sequence of the heavy chain CDR1 (SEQ ID NO: 1) of anti-ED-A F8 antibody is underlined. The amino acid sequence of the heavy chain CDR2 (SEQ ID NO: 2) of the anti-ED-A F8 antibody is shown in italics and underlined. The amino acid sequence of the heavy chain CDR3 (SEQ ID NO: 3) of anti-ED-A antibody F8 is shown in bold and underlined. FIG. 1B shows the amino acid sequence of the anti-ED-A F8 antibody linker sequence between the VH and VL domains (SEQ ID NO: 9). FIG. 1C shows the amino acid sequences of the anti-ED-A F8 antibody light chain (VL) (SEQ ID NO: 8). The amino acid sequence of the light chain CDR1 (SEQ ID NO: 4) of the anti-ED-A F8 antibody is underlined. The amino acid sequence of the light chain CDR2 (SEQ ID NO: 5) of the anti-ED-A F8 antibody is shown in italics and underlined. The amino acid sequence of the light chain CDR3 (SEQ ID NO: 6) of anti-ED-A F8 antibody is shown in bold and underlined. FIG. 1D shows the amino acid sequence of the linker between the F8 antibody and IL-10 when the antibody is conjugated to IL-10. FIG. 1E shows the amino acid sequence of human IL-10.

FIG. 4A-4D shows the cytokine levels in mice treated with F8-4,10. The above chart represents the cytokine levels in the serum of healthy mice (water), diseased mice which received no treatment (3% DSS), diseased mice which received F8 antibody in Small Immune Protein format (F8SIP), diseased mice which received F8-IL10 (F8-IL10). The cytokine levels (expressed as pg of protein per ml of serum) reported are: Interleukin 1β, (IL1-b) (FIG. 4A), Interleukin 12 (IL-12p70) (FIG. 4B), Interferon γ (IFNγ) (FIG. 4C) and Interleukin 6 (IL6) (FIG. 4D).

FIG. 5A-5C shows the cytokine levels in mice treated with F8-IL10. The above chart represents the cytokine levels in the serum of healthy mice (water), diseased mice which received no treatment (3% DSS), diseased mice which received F8 antibody in Small Immune Protein format (F8SIP), diseased mice which received F8-IL10 (F8-IL10). The cytokine levels (whose levels were expressed as pg of protein per ml of serum) reported are: Keratinocyte-derived chemohine (KC) (FIG. 5A), Interleukin 1© (IL10) (FIG. 5C) and Tumor Necrosis Factor alpha (TNFa) (FIG. 5B).

FIG. 6A-6B shows histochemical analysis of specimens of colon tissue from patients affected by ulcerative colitis (FIG. 6A) and by Crohn's disease (FIG. 6B) probed with the F8 antibody in SIP format and the Von Willebrand factor. The staining pattern observed with the F8 antibody and the Von Willebrand factor shows that the F8 stains the newly formed blood vessels but not the normal blood vessels in patients affected by ulcerative colitis and Crohn's disease. (Von Willebrand factor is routinely used as a marker of normal vasculature.)

FIG. 7A-7D shows histochemical analysis of specimens of colon tissue of patients affected by ulcerative colitis (FIG. 7B) and by Crohn's disease (FIG. 7D) and of non-affected colons (FIG. 7A, 7C). The staining pattern observed with the F8 antibody shows that the F8 stains more intensely the new forming blood vessels in the diseased colons.

TERMINOLOGY

Fibronectin

Figure 2:
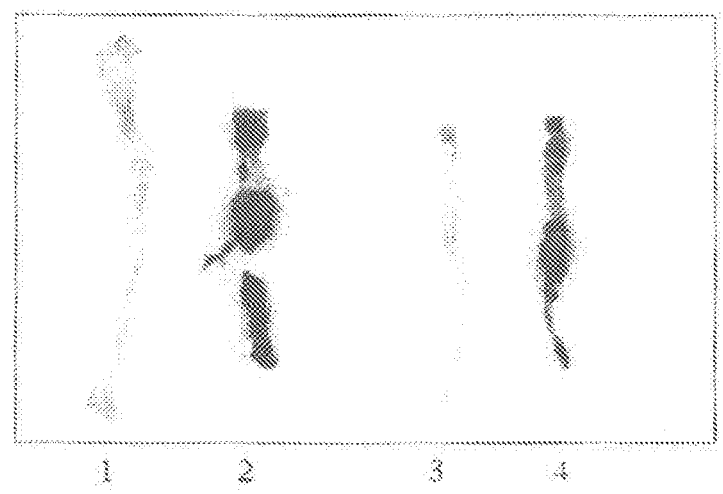
FIG. 2 shows the results of a colon autoradiography from IBD and healthy mice. Colons were harvested and exposed to a phosphor-imaging screen (Molecular Dynamics) for 24 hours, and imaging via Storm 860. Lane-1; colon harvested at 6-hr post injection from Group 0 (healthy mouse); Lane-2: colon harvested at 6-hr post injection from Group 2 (IBD mouse); Lane-3: colon harvested at 24-hr post injection from Group 0 (healthy mouse); Lane-4: colon harvested at 24-hr past injection Group 2 (IBD mouse).

Fibronectin is an antigen subject to alternative splicing, and a number of alternative isoforms of fibronectin are known, as described elsewhere herein. Extra Domain-A (EDA or ED-A) is also known as ED, extra type III repeat A (EIIIA), or EDI. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276. The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN (Borsi et al., 1987, J. Cell Biol., 104, 595-600). ED-A is mainly absent in the plasma form of FN but is abundant during embryogenesis, tissue remodelling, fibrosis, cardiac transplantation and solid tumour growth.

Alternative Splicing

Alternative splicing refers to the occurrence of different patterns of splicing of a primary RNA transcript of DNA to produce different mRNAs. After excision of introns, selection may determine which exons are spliced together to form the mRNA. Alternative splicing leads to production of different isoforms containing different exons and/or different numbers of exons. For example one isoform may comprise an additional amino acid sequence corresponding to one or more exons, which may comprise one or more domains.

Specific Binding Member

This describes one member of a pair of molecules that bind specifically to one another. The members of a specific binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A specific binding member normally comprises a molecule having an antigen-binding site. For example, a specific binding member may be an antibody molecule or a non-antibody protein that comprises an antigen-binding site. A specific binding member, as referred to herein, is preferably an antibody molecule.

An antigen binding site may be provided by seeds of arrangement of complementarity determining regions (CDRs) on non-antibody protein scaffolds such as fibronectin or cytochrome B etc. (Haan & Maggos, (2004), BioCentury, 12(5): A1-A6; Koide et al., (1998), Journal of Molecular Biology, 284; 1141-1151; Nygren et al., (1997), Current Opinion in Structural Biology, 7; 463-469), or by randomising or mutating amino acid residues of a loop within a protein scaffold to confer binding specificity for a desired target. Scaffolds for engineering novel binding sites in proteins have been reviewed in detail by Nygren et al. (1997) (Current Opinion in Structural Biology, 7: 463-469). Protein scaffolds for antibody mimics are disclosed in WO/00347784, in which the inventors describe proteins (antibody mimics) that include fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigens. Use of antigen binding sites in non-antibody protein scaffolds is reviewed in Wess, 2004, In: BioCentury, The Bernstein Report on BioBusiness, 12(42), A1-A7. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyolotides—small proteins having intra-molecular disulphide bonds.

In addition to antibody sequences and/or an antigen-binding site, a specific binding member for use in the present invention may comprise other amino acids, e.g., forming a peptide or polypeptide, such as a folded domain, or to impart to the molecule another functional characteristic in addition to ability to bind antigen. Binding members for use in the invention may carry a detectable label, or may be conjugated to a toxin, a molecule that exerts immunosuppressive or anti-inflammatory effect or a targeting moiety or enzyme (e.g. via a peptidyl bond or linker). Preferably, a binding members for use in the invention is conjugated to interleukin 10.

For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations or immunoglobulin variable domains may be determined by reference to Kabat et al. (1987) (Sequences of Proteins of Immunological Interest, 4th Edition, US Department of Health and Human Services.), and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987) Sequences of Proteins of Immunological Interest, 4$^{th}$ Edition, US Department of Health and Human Services (Kabat et al., (1991a), Sequences of Proteins of Immunological Interest, 5$^{th}$ Edition, US Department of Health and Human Services, Public Service, NIH, Washington, and later editions). An antibody typically contains 3 heavy chain CDRs and 3 light chain CDRs. The term CDR or CDRs is used here in order to indicate, according to the case, one of these regions or several, or even the whole, of these regions which contain the majority at the amino acid residues responsible for the binding by affinity of the antibody for the antigen or the epitope which it recognizes.

Among the six short CDR sequences, the third CDR of the heavy chain (HCDR3) has a greater site variability (greater diversity essentially due to the mechanisms of arrangement or the genes which give rise to it). It can be as short as 2 amino acids although the longest size known is 26. Functionally, HCDR3 plays a role in part in the determination of the specificity of the antibody (Segal et al., (1974), PNAS, 71: 4298-4302; Amit et al., (1986), Science, 233: 747-753; Chothia et al., (1987) J. Mol. Biol., 196; 901-917; Chothia et al., (1989), Nature, 342: 877-883; Caton et al., (1990), J. Immunol., 144: 1965-1968; Sharon et al., (1990a), PNAS, 87: 4814-4817; Sharon et al., (1990b), J. Immunol., 144: 4863-4869; Kabat et al., (1991b), J. Immunol., 147: 1709-1719).

Antibody Molecule

This describes an immunoglobulin whether natural or partly or wholly synthetically produced. The term also relates to any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by generic recombination, or by chemical synthesis, and that they can then contain unnatural amino acids as will be described later. Antibody fragments that comprise an antibody antigen-binding site include, but are not limited to, antibody molecules such as Fab, Fab', fab'-SH, scFv, Fv, dAb, Fd; and diabodies.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included.

Cloning and expression of chimeric antibodies are described in EP-A-0120694 and EPA-A-0125023, and a large body of subsequent literature.

Further techniques available in the art of antibody engineering have made it possible to isolate human and humanised antibodies. For example, human hybridomas can be made as described by Kontermann & Dubel (2001), S. *Antibody Engineering*, Springer-Verlag New York, LLC; ISBN: 3540413545. Phage display, another established technique for generating binding members has been described in detail in many publications such as WO92/01047 (discussed further below) and U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,692,255, U.S. Pat. No. 6,140,471, U.S. Pat. No. 6,172,197, U.S. Pat. No. 6,225,447, U.S. Pat. No. 6,291,650, U.S. Pat. No. 6,492,160, U.S. Pat. No. 6,521,404 and Kontermann & Dubel (2001), S, *Antibody Engineering*, Springer-Verlag New York, LLC; ISBN: 3540413545. Transgenic mice in which the mouse antibody genes are inactivated and functionally replaced with human antibody genes while leaving intact other components of the mouse immune system, can be used for isolating human antibodies (Mendez et al., (1997), Nature Genet, 15(2): 146-156).

Synthetic antibody molecules may be created by expression from genes generated by means of oligonucleotides synthesized and assembled within suitable expression vectors, for example as described by Knappik et al. (2000) J. Mol. Biol. 296, 57-86 or Krebs et al. (2001) Journal of Immunological Methods, 254 67-84.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-555; Holt et al. (2003) Trends in Biotechnology 21, 484-490), which consists of a VH or a VL domain; (v) isolated CDR regions; (vi) F(ab') 2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245), Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments for use in the invention can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments of the present invention may be obtained by techniques of genetic recombination likewise well known to the person skilled in the art or else by peptide synthesis by means of, for example, automatic peptide synthesizers such as these supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain (Holt et al. (2003) Trends in Biotechnology 21, 484-490). VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A binding member of the present invention may be a dAb comprising a VH or VL domain substantially as set out herein, or a VH or VL domain comprising a set of CDRs substantially as set out herein.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

Bispecific or bifunctional antibodies form a second generation of monoclonal antibodies in which two different variable regions are combined in the same molecule (Holliger and Bohlen 1999 Cancer and metastasis rev. 18: 411-419). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger et al. (1993b), Current Opinion Biotechnol 4, 446-449), e.g. prepared chemically or from hybrid hybridomas, or may be any of the biospecific antibody fragments mentioned above. These antibodies can be obtained by chemical methods (Glennie et al., (1987) J. Immunol. 139, 2367-2375; Repp et al., (1995) J. Hemat. 377-332) or somatic methods (Staerz U. D. and Bevan M. J. (1986) PNAS 83; Suresh et al. (1986) Method. Enzymol. 121: 210-228) but likewise by genetic engineering techniques which alloy the heterodimerization to be forced and thus facilitate the process of purification of the antibody sought (Merchand et al., 1998 Nature Biotech. (16:677-6681). Examples of bispecific antibodies include those of the BiTE™ technology in which the binding domains of two antibodies with different specificity can be used and directly linked via short flexible peptides. This combines two antibodies on a short single polypeptide chain.

Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because whey can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against a target antigen, then a library can be made where the other arm is varied and an antibody of appropriate specificity selected. Bispecific whole antibodies may be made by alternative engineering methods as described in Ridgeway et al. (1996), Protein Eng., 9, 616-621.

Various methods are available in the art for obtaining antibodies against a target antigen. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein, 1975, Nature, 256:495-497.

Monoclonal antibodies can be obtained, for example, from an animal cell immunized against A-FN, or one of its fragments containing the epitope recognized by said monoclonal antibodies, e.g. a fragment comprising or consisting of ED-A, or a peptide fragment of ED-A. The A-FN, or one of their fragments, can especially be produced according to the usual working methods, by genetic recombination starting with a nucleic acid sequence contained in the cDNA sequence coding for A-FN, or fragment thereof, by peptide synthesis starting from a sequence of amino acids comprised in the peptide sequence of the A-FN and/or fragment thereof.

Monoclonal antibodies can, for example, be purified on an affinity column on which A-FN, or one of their fragments containing the epitope recognized by said monoclonal antibodies, e.g. a fragment comprising or consisting of ED-A, or a peptide fragment of ED-A, has previously been immobilized. Monoclonal antibodies can be purified by chromatography on a protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. The whole of these techniques may be used simultaneously or successively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated

This refers to the state in which specific binding members for use in the invention or nucleic acid encoding such specific binding members, will generally be in accordance with the present invention. Thus, specific binding members, VH and/or VL domains of the present invention my be provided isolated and/or purified, e.g. from their natural environment, in substantially pure or homogeneous form, or, in the case of the nucleic acid, free or substantially free of nucleic acid or genes of origin other than the sequence encoding a polypeptide with the required function. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Specific binding members and nucleic acid may be formulated with diluents or adjuvants and sill for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems or heterologous eukaryotic cells (e.g. CHO or NS-0 (ECACC 85110503) cells, or they may be (for example if produced by expression in a prokaryotic cell) unglucosylated.

Heterogeneous preparations comprising antibody molecules may also be used in the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

One or more specific binding members for an antigen, e.g. the A-FN, the ED-A of fibronectin, may be obtained by bringing into contact a library of specific binding members according to the invention and the antigen or a fragment thereof, e.g. a fragment comprising or consisting of ED-A, or a peptide fragment of ED-A and selecting one or more specific binding members of the library able to bind the antigen.

An antibody library may be screened using Iterative Colony Filter Screening (ICFS). In ICFS, bacteria containing the DNA encoding several binding specificities are grown in a liquid medium and, once the stage of exponential growth has been reached, some billions of them are distributed onto a growth support consisting of a suitably pretreated membrane filter which is incubated until completely confluent bacterial colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped. The trap membrane is then treated to point out bound antibody fragments scFv with colorimetric techniques commonly used to this purpose.

The position of the coloured spots on the trap filter allows one to go back to the corresponding bacterial colonies which are present on the growth membrane and produced the antibody fragments trapped. Such colonies are gathered and grown and the bacteria—a few millions of them are distributed onto a new culture membrane repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO0246455.

A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO092/01047 and e.g. U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160 and U.S. Pat. No. 6,521,404.

Following selection of binding members able to bind the antigen and displayed on bacteriophage or other library particles or molecular complexes, nucleic acid may be taken from a bacteriophage or other particle op molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind the A-FN, or the ED-A of fibronectin, or other target antigen or isoform may be further tested, e.g. ability to compete with anti-ED-A antibody F8 for binding to the A-FN or a fragment of the A-FN, e.g. the ED-A of fibronectin.

A specific binding member for use in the invention may bind the A-FN and/or the ED-A of fibronectin specifically. A specific binding member of the present invention may bind the A-FN and/or the ED-A of fibronectin, with the same affinity as anti-ED-A antibody F8 e.g. in scFv format, or with an affinity that is better. A specific binding member for use in the invention may bind the A-FN and/or the ED-A of fibronectin, with a $K_D$ and $3 \times 10^{-8}$ M or an affinity that is better. Preferably, a specific binding member for use in the invention binds the A-FN and/or the ED-A of fibronectin, with a $K_D$ if $2 \times 10^{-8}$ M or an affinity that is better. More preferably, a specific binding member for use in the invention binds the A-FN and/or the ED-A of fibronectin, with a $K_D$ of $1.7 \times 10^{-8}$ M or an affinity that is better. yet more preferably, a specific binding member for use in the invention binds the A-FN and/or the Ed-A of fibronectin, with a $K_D$ of $1.4×10^{-8}$ M or an affinity that is better. Most preferably, a specific binding member for use in the invention binds the A-FN and/or the ED-A of fibronectin, with a $K_D$ of $3×10^{-9}$ M or an affinity that is better.

A specific binding member of the present invention may bind to the same epitope on A-FN and/or the ED-A of fibronectin anti-ED-A antibody F8.

A specific binding member for use in the invention may not show any significant binding to molecules other than to the A-FN and/or the ED-A or fibronectin. In particular, the specific binding member may not bind other isoforms of fibronectin, for example the ED-B isoform and/or the IIICS isoform of fibronectin.

Variants of antibody molecules disclosed herein may be produced and used in the present invention. The techniques required to make substitutions within amino acid sequences of CDRs, antibody VH or VL domains, in particular the framework regions of the VH and VL domains, and binding members generally are available in the art. Variant sequences may be made, with substitutions that may or may not be predicted to have a minimal or beneficial effect on activity, and tested for ability to bind A-FN and/or the ED-A of fibronectin, and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, maybe 5, 4, 3, 2 or 1. Alterations may be made in one or more framework regions and/or one or more CDRs. The alterations normally do not result in loss of function, so a specific binding member comprising a thus-altered amino acid sequence may retain an ability to bind A-FN and/or the ED-A of fibronectin. For example, it may retain the same quantitative binding as a specific binding member in which the alteration is not made, e.g. as measured in an assay described herein. The specific binding member comprising a thus-altered amino acid sequence may have an improved ability to bind A-FN and/or the ED-A of fibronectin. For example, a specific binding member that binds the ED-A isoform or ED-A of fibronectin, as referred to herein, may comprise the VH domain shown in SEQ ID NO: 7 and the VL domain shown in SEQ ID NO: 8 with 10 or fewer, for example, 5, 4, 3, 2 or 1 amino acid substitution within the framework region of the VH and/or VL domain. Such a specific binding member may bind the ED-A isoform or ED-A of fibronectin with the same or substantially the same, affinity as a specific binding member comprising the VH domain shown in SEQ ID NO: 7 and the VL domain shown in SEQ ID NO: 8 or may bind the ED-A isoform or ED-A of fibronectin with a higher affinity than a specific binding member comprising the VH domain shown in SEQ ID NO: 7 and the VL domain shown in SEQ ID NO:8.

Novel VH or VL regions carrying CDR-derived sequences for use in the invention may be generated using random mutagenesis of one or more selected VH and/or VL genes to generate mutations within the entire variable domain. In some embodiments one or two amino acid substitutions are made within an entire variable domain or set of CDRs. Another method that may be used is to direct mutagenesis to CDR regions of VH or VL genes.

As noted above, a CDR amino acid sequence substantially as set out herein may be carried as a CDR in a human antibody variable domain or a substantial portion thereof. The HCDR3 sequences substantially as set out herein represent embodiments of the present invention and for example each of these may be carried as a HCDR3 in a human heavy chain variable domain or a substantial portion thereof.

Variable domains employed in the invention may be obtained of derived from any germ-line or rearranged human variable domain, or may be a synthetic variable domain based on consensus or actual sequences of known human variable domains. A variable domain can be derived from a non-human antibody. A CDR sequence for use in the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members for use in the invention. The repertoire may then be displayed in a suitable host system such as the phage display system of WO92/01047, or any of a subsequent large body of literature, including Kay, Winter & McCafferty (1996), so that suitable binding members may be selected. A repertoire may consist of from anything from $10^4$ individual members upwards, for example at least $10^5$, at least $10^6$, at least $10^7$, at least $10^8$, at least $10^9$, or at least $10^{10}$ members.

Similarly, one or more, or all three CDRs may be grafted into a repertoire of VH or VL domains that are then screened for a binding member or binding members for the A-FN and/or the ED-A of fibronectin.

One or more of the HCDR1, HCDR2, and HCDR3 of antibody F8 or the set of HCDRs of antibody F8 may be employed, and/or one or more of the LCDR1, LCDR2 and LCDR3 of antibody F8 the set of LCDRs of antibody F8 may be employed.

Similarly, other VH and VL domains, sets of CDRs and sets of HCDRs and/or sets of LCDRs disclosed herein may be employed.

The A-FN and/or the ED-A of fibronectin may be used in a screen for specific binding members, e.g. antibody molecules, for use in the preparation of a medicament for the treatment of IBD. The screen may a screen of a repertoire as disclosed elsewhere herein.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains disclosed elsewhere herein to further protein sequences including antibody constant regions, other variable domains (for example in the production of diabodies) or detectable/ functional labels as discussed in more detail elsewhere herein.

Although specific binding members may comprise a pair of VH and VL domains, single binding domains based on either VH or VL domain sequences may also be used in the invention. It is know that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind A-FN and/or the ED-A of fibronectin. This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain binding member is selected in accordance with phage display techniques such as those described in that reference. This technique is also disclosed in Marks 1992.

Specific binding members for use in the present invention may further comprise antibody constant regions or parts thereof, e.g. human antibody constant regions or parts thereof. For example, a VL domain may be attached at its C-terminal end to antibody light chain constant domains including human Cκ or Cλ chains, e.g. Cλ. Similarly, a specific binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes classes, particularly IgG1 and IgG4. Any synthetic or other constant region variant that has these properties and stabilizes variable regions is also useful in embodiments of the present invention.

Specific binding members for use in the invention may be labelled with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance. Detectable labels may be attached to antibodies for use in the invention using conventional chemistry known in the art.

There are numerous methods by which the label can produce a signal detectable by external means, for example, by visual examination, electromagnetic radiation, heat, and chemical reagents. The label can also be bound to another specific binding member that binds the antibody for use in the invention, or to a support.

Labelled specific binding members, e.g. scFv labelled with a detectable label, may be used diagnostically in vivo, ex vivo or in vitro, and/or therapeutically.

For example, radiolabelled binding members (e.g. binding members conjugated to a radioisotope) may be used in radiodiagnosis and radiotherapy. Radioisotopes which may be conjugated to a binding member for use in the invention include isotopes such as $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{123}$I, $^{124}$I, $^{125}$I, $^{131}$I, $^{18}$F, $^{211}$At and $^{225}$Ac. Preferably, positron emitters, such as $^{18}$F and $^{124}$I, or gamma emitters, such as $^{99m}$Tc, $^{111}$In and $^{123}$I, are used for diagnostic applications (e.g. for PET), while beta-emitters, such as $^{131}$I, $^{90}$Y, and $^{177}$Lu, are preferably used for therapeutic applications. Alpha-emitters, such as $^{211}$At and $^{225}$Ac may also be used for therapy.

For example, a specific binding member for use in the invention labelled with a detectable label may be used to detect, diagnose or monitor IBD in a human or animal.

A specific binding member of the present invention may be used for the manufacture of a diagnostic product for use in diagnosing IBD.

A conjugate or fusion between a binding member for use in the invention and a molecule that exerts a biocidal, cytotoxic immunosuppressive or anti-inflammatory effect on target cells in the lesions and an antibody directed against an extracellular matrix component which is present in such lesions may be employed in the present invention. For example, the conjugated molecule may be interleukin-10. Such conjugates may be used therapeutically, e.g. for treatment of IBD as referred to herein.

Production and use of fusions or conjugates of specifics binding members with biocidal or cytotoxic molecules is described for example in WO01/62298.

The specific binding member for use in the invention may be a conjugate of (i) a molecule which exerts an anti-inflammatory effect on target cells by cellular interaction, an anti-inflammatory molecule, a cytokine e.g. IL-10 and (ii) a specific binding member for the ED-A isoform of fibronectin and/or the ED-A of fibronectin.

The specific binding member for use in the invention may be a conjugate of (i) a molecule which exerts an immunosuppressive or anti-inflammatory effect and (ii) a specific binding member for the ED-A isoform of fibronectin and/or the ED-A of fibronectin.

The specific binding member for use in the invention is preferably a conjugate of (i) interleukin-10 (IL10) and (ii) a specific binding member for the ED-A isoform of fibronectin and/or the Ed-A of fibronectin. Such a specific binding member is useful in aspects of the invention disclosed herein relating to treatment of IBD.

Also described herein is a conjugate of (i) a molecule which exerts a biocidal or cytotoxic effect on target cells by cellular interaction, or an immunosuppressive or anti-inflammatory effect and (ii) a binding member for the ED-A isoform of fibronectin and/or the ED-A of fibronectin. Such a conjugate preferably comprises a fusion protein comprising the biocidal, cytotoxic, immunosuppressive or anti-inflammatory molecule and a said binding member, or, where the binding member is two-chain or multi-chain, a fusion protein comprising the biocidal, cytotoxic, immunosuppressive or anti-inflammatory molecule and a polypeptide chain component of said binding member. Preferably the binding member is a single-chain polypeptide, e.g. a single-chain antibody molecule, such as scFv.

A conjugate, as referred to herein, may be expressed as a fusion protein. Thus, a fusion protein comprising the immunosuppressive or anti-inflammatory molecule and a single-chain Fv antibody molecule may be used in the invention.

The immunosuppressive or anti-inflammatory molecule that exerts its effect on target cells by cellular interaction, may interact directly with the target cells, may interact with a membrane-bound receptor on the target cell or perturb the electrochemical potential of the cell membrane. Preferably, the molecule is IL-10.

Preferably, the molecule which is conjugated to the specific binding member is IL-10.

As discussed further below, the specific binding member for use in the invention is preferably an antibody molecule or comprises an antibody antigen-binding site. Conveniently, the specific binding member may be a single-chain polypeptide, such as a single-chain antibody. This allows for convenient production of a fusion protein comprising single-chain antibody and, for example, immunosuppressive or anti-inflammatory molecule (e.g. interleukin-10 or TGF beta). An antibody antigen-binding site may be provided by means of association of an antibody VH domain and an antibody VL domain in separate polypeptides, e.g. in a complete antibody or in an antibody fragment such as Fab or diabody. Where the specific binding member is a two-chain or multi-chain molecule (e.g. Fab or whole antibody, respectively), an immunosuppressive or anti-inflammatory molecule, for example, may be conjugated as a fusion polypeptide with one or more polypeptide chains in the specific binding member.

The specific binding member may be conjugated with the immunosuppressive or anti-inflammatory molecule by means of a peptide bond, i.e. within a fusion polypeptide comprising said molecule and the specific binding member or a polypeptide chain component thereof (see e.g. Trachsel et al.). Other means for conjugation include chemical conjugation, especially cross-linking using a bifunctional reagent (e.g. employing DOUBLE-REAGENTS™ Cross-linking Reagents Selection Guide, Pierce).

Also provided is an isolated nucleic acid encoding a specific binding member for use in the present invention. Nucleic acid may include DNA and/or RNA. A nucleic acid may code for a CDR or set of CDRs or VH domain or VL domain or antibody antigen-binding site or antibody molecule, e.g. scFv or IgG, e.g. IgG1, as defined above. The nucleotide sequences may encode the VH and/or VL domains disclosed herein.

Further described herein are constructs in the form of plasmids, vectors, transcription or expression cassettes which comprise at least one polynucleotide as described above.

A recombinant host cell that comprises one or more constructs as above are also provided. A nucleic acid encoding any CDR or set of CDRs or VH domain or VL domain or antibody antigen-binding site or antibody molecule, e.g. scFv or IgG1 or IgG4 as provided, is described, as is a method of production of the encoded product, which method comprises expression from encoding nucleic acid. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

A nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A method of production of an antibody VH variable domain, the method including causing expression from encoding nucleic acid is also described. Such a method may comprise culturing host cells under conditions for production of said antibody VH variable domain.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun (1991), Bio/Technology 9: 545-551. A common bacterial host is *E. coli*.

Expression in eukaryotic cells in culture is also available to those skilled in the art as an option for production of a specific binding member for example Chadd et al. (2001), Current Opinion in Biotechnology 12: 188-194); Andersen et al. (2002) Current Opinion in Biotechnology 13: 117; Larrick & Thomas (2001) Current Opinion in Biotechnology 12: 411-418. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001) *Molecular Cloning: a Laboratory Manual:* 3rd edition, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. (1999) $4^{th}$ eds., *Short Protocols in Molecular Biology: A Compendium of Methods from Current Protocols in Molecular Biology*, John Wiley & Sons.

A host cell may contain a nucleic acid as described herein. Such a host cell may be in vitro and may be in culture. Such a host cell may be in vivo. In vivo presence of the host cell may allow intracellular expression of a binding member for use in the present invention as "intrabodies" or intracellular antibodies. Intrabodies may be used for gene therapy.

A method comprising introducing a nucleic acid disclosed herein into a host cell is also described. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

The nucleic acid may be integrated into the genome (e.g. chromosome) of the host cell. Integration may be promoted by inclusion of sequences that promote recombination with the genome, in accordance with standard techniques.

A method that comprises using a construct as stated above in an expression system in order to express a specific binding member or polypeptide as above is also described.

Specific binding members for use in the present invention are designed to be used in methods of diagnosis or treatment in human or animal subjects, e.g. human. Specific binding members for use in the invention may be used in diagnosis or treatment of IBD.

Accordingly, the invention provides methods of treatment comprising administration of a specific binding member as described, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient. Pharmaceutically acceptable vehicles are well known and will be adapted by the person skilled in the art as a function of the nature and of the mode of administration of the active compound(s) chosen.

Specific binding members for use in the present invention will usually be administered in the form of a pharmaceutical composition, which may comprise at least one component in addition to the specific binding member. Thus, pharmaceutical compositions described herein, and for use in accordance with the present invention, may comprise, in addition to active ingredient, a pharmaceutically acceptable excipient, carrier, buffer, stabilizer or other materials well know to those skilled in the art. Such materials should be non-toxic and should not interfere with the efficacy of the active ingredient. The precise nature of the carrier or other material will depend on the route of administration, which may be oral, inhaled or by injection, e.g. intravenous.

Pharmaceutical compositions for oral administration such as for example nanobodies etc are also envisaged in the present invention. Such oral formulations may be in table, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson ed., Sustained and Controlled Release Drug Delivery Systems, Marcel Dekker, Inc., New York, 1978.

A composition may be administered alone or in combination with other treatments, concurrently or sequentially or as a combined preparation with another therapeutic agent or agents, dependent upon the condition to be treated.

A specific binding member for use in the present invention may be used as part of a combination therapy in conjunction with an additional medicinal component. Combination treatments may be used to provide significant synergistic effects, particularly the combination of a specific binding member for use in the present invention with one or more other drugs. A specific binding member for use in the present invention may be administered concurrently or sequentially or as a combined preparation with another therapeutic agent or agents, for the treatment of one or more of the conditions listed herein.

For example, a specific binding member for use in the invention may be used in combination with an existing therapeutic agent for the treatment of IBD.

A specific binding member for use in the invention and one or more of the above additional medicinal components may be used in the manufacture of a medicament. The medicament may be for separate or combined administration to an individual, and accordingly may comprise the specific binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration may be in a "therapeutically effective amount", this being sufficient to show benefit to a patient. Such benefit may be at least amelioration of at least one symptom. Thus "treatment of IBD" refers to amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of specific binding member, the method of administration, the scheduling of administration and other factors known to medical practitioners. Prescription of treatment, e.g. decisions on dosage etc, is within the responsibility of general practitioners and other medical doctors, and may depend on the severity of the symptoms and/or progression of a disease being treated. Appropriate doses of antibody are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for the type of medicament being administered, may be used. A therapeutically effective amount or suitable dose of a specific binding member for use in the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody), and the nature of any detectable label or other molecule attached to the antibody. A typical antibody dose will be in the range 100 µg to 1 g for systemic applications, and 1 µg to 1 mg for topical applications. An initial higher loading dose, followed by one or more lower doses, may be administered. An antibody may be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

Inflammatory Bowel Disease (IBD)

Inflammatory Bowel Disease is a group of inflammatory conditions that affect the colon and small intestine. The major types of IBD are Crohn's disease (CD) and ulcerative colitis (UC), while other types of IBD include collagenous colitis, lymphocytic colitis, ischaemic colitis, diversion colitis, Behçet's disease and indeterminate colitis. CD can affect any part of the gastrointestinal tract, whereas UC is typically restricted to the colon and rectum. IBD, as referred to herein, may be CD, UC, collagenous colitis, lymphocytic colitis, ischaemic colitis, diversion colitis, Behçet's disease or indeterminate colitis. In particular, the terms CD, UP, collagenous colitis, lymphocytic colitis, ischaemic colitis, diversion colitis, Behçet's disease and indeterminate colitis, as used herein, may refer to active CD, active UC, active collagenous colitis, active lymphocytic colitis, active ischaemic colitis, active diversion colitis, active Behçet's disease and active indeterminate colitis, respectively. In one embodiment, the IBD may be CD or UC. In another embodiment, the IBD may be CD, collagenous colitis, lymphocytic colitis, ischaemic colitis, diversion colitis, Behçet's disease or indeterminate colitis. In a further embodiment, the IBD is not UC. The IBD may be an IBD which is not typically restricted to inflammation in the colon and the rectum, such as CD. The IBD may be an IBD which does not affect only the lining of the colon. In a preferred embodiment, the IBD is CD. Most preferably, the IBD is active CD.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL

Materials and Methods

Mouse IBD Model

Mouse models for IBD which involve the administration of DSS are known in the art. A suitable mouse model is also described, for example, in Okayasu et al. (1990), Gastroenterology, 98, 694-702.

For the experiments described herein, colitis was induced in C57BL/6 mice (Jackson Laboratories, Bar Harbor, Me.) by inclusion of 3% dextran sodium sulfate (DSS) (MP BioMedicals) into drinking water for 7 days followed by 3-5 days of normal drinking water. Control mice were given standard water throughout the course of the study. Mice were monitored for disease induction/progression as evidenced by hemoccult on days 3-5 as well as by daily weight change. Mice were euthanized at various times 3-5 days following cessation of DSS in the water to evaluate targeting, localization and pharmacological effects of F8-IL-10

$^{125}$I-F8/IL10 Radioiodination, Purification, Characterization and Dosing Solution Preparation $^{125}$I-F8/IL10 was prepared using Succinimidyl-iodobenzoate (SIB) (Zalutsky & Narula (1988) Cancer Research, 48, 1446-1450; Zalutsky & Narula (1987) Appl. Radiat. Isot. 38, 1051-1055; Cheng, et al. (2002) *J. Med. Chem.* 45, 3048-3056). Briefly, an aliquot of Iodine-125 (20 µL~2.0 mCi) (Perkin Elmer, Waltham, Mass.) was reacted with 2.5 µg N-Succinimidyl-3-(tri-n-butylstannyl) benzoate ($C_{23}H_{35}NO_4Sn$; MW=508.23, synthesized by Texas Biochemicals, Inc. College Station, Tex.) together with 10 µg NCS (Sigma-Aldrich, St. Louis, Mo.) as an oxidant in 50 µL of methanol containing 1.5% acetic acid (v:v) (both from Sigma-Aldrich). After 15 min incubation at ambient temperature, the remaining oxidant in reaction solution was quenched by adding 10 µg sodium bisulfate (reducing agent) (Sigma-Aldrich) and incubating at ambient temperature for an additional 5 min. The $^{125}$I-labeled SIB was conjugated to the F8-IL10 antibody (~0.2 mg, with a starting molar ratio of approximately 2.5:1 for intermediate to antibody) by incubating at ambient temperature for 20 min at pH 8.0. The radiolabeled product ($^{125}$I-F8/IL10) was purified using a pre-balanced PD-10 column (GE Healthcare, Little Chalfont, Buckinghamshire, UK) (potential non-specific protein binding sites on the column were saturated using bovine serum albumin, followed by rinsing the column with at least three column volumes of PBS), eluted in PBS. A radiochemical yield of approximately 30% was obtained.

The radiochemical purity (RCP) and bioactivity of $^{125}$I-F8/IL10 were characterized via size exclusion chromatogram (SEC), and EDA-affinity column, respectively. For SEC analysis, approximately 1 µCi of $^{125}$I-F8/IL10 product solution was injected into the HPLC (Agilent 1100, equipped with an in-line radioactive detector) equipped with a size exclusion column (G3000SW×1, TOSOH Biosciences, Tokyo, Japan) and eluted with a flow rate of 1 mL per minute with mobile solvent of 25 MM phosphate buffer, 0.15 M NaCl, pH 6.8. The identity of $^{125}$I-F8/IL10 was confirmed by comparing its retention time in radiometric chromatogram to that of the reference F8/IL10 in UV (280 nm) chromatogram. An RCP of greater than 99% was obtained for $^{125}$I-F8/IL10, with a radioactive specific activity of approximately 4.5 mCi/mg.

The bioactivity of $^{125}$I-F8-IL10 was determined via an EDA affinity column assay. Briefly, an aliquot (approximately 1 µCi) of $^{125}$I-F8/IL10 was loaded on a pre-balanced EDA affinity column (containing 250 µL of EDA resin, the pre-balance was conducted by blocking the non-specific binding sites with 2 mL BSA, 2 mg/mL in PBS, and then by washing the column with 8 mL PBS). The affinity column was washed with 6 mL of BSA (2 mg/mL in PBS) and one eluate was fractionally collected. The radioactivity in the collected eluate and remaining on the affinity column was measured in a gamma counter. The percentage of radioactivity retained in the EDA-resin column out of total loaded radioactivity was calculated. A percentage of 64% of radioactivity retained in the affinity column was obtained for $^{125}$I-F8/IL10.

The dosing solutions used for PK and tissue distribution studies were prepared by mixing $^{125}$-F8/IL10 with unlabeled F8/IL10 (F8/IL10 stock solution), and formulation buffer to the required final concentration. The test article solution was prepared on the day of dosing and brought to ambient temperature prior to administration to the animals.

$^{125}$I-F8/IL10 Biodistribution and Localization to Colon in IBD Mouse Model Untreated or DSS-treated mice were both treated with potassium iodide (KI) water (20 mM) approximately 2-4 days prior to the dosing (day 5-7 following initiation of DSS) to block the thyroid uptake of any potential unbound free I-125 generated in vivo. On day 9 following initiation of DSS treatment, a single dose of $^{125}$-F8/IL10 was administered intravenously (IV). The dose and radioactivity per group is outlined below:
   i) Group 0—approximate dose per mouse; 5 mg/kg
      Group 0—approximate radioactivity per mouse: 7.5 µCi (specific activity 75 uCi/mg).
   (ii) Group 1—approximate dose per mouse: 5 mg/kg
      Group 1—approximate radioactivity per mouse; 10 µCi (specific activity 100 uCi/mg).
   iii) Group 2—approximate doses per mouse: 0.15 mg/kg,
      Group 2—approximate radioactivity per mouse: 12 µCi (specific activity 4490 uCi/mg).

Subgroups of mice were bled at 5 minutes, 1, 3, 6, 24, 48 and 96 hours and then various tissues were collected. Blood samples were collected either to cardiac puncture or retroorbital bleeding into serum separator collection tubes. Serum samples were harvested by centrifugation of the blood samples at 10,000 g for 5 min. For tissue collection, the animal was sacrificed and tissues of interest were collected immediately after blood sampling and whole body perfusion. The whole body blood perfusion was conducted by administering approximately 20 mL of heparin-PBS (25 units per mL) for approximately 10 min. The tissues of interest included brain, mesenteric lymph nodes, skin, fat, skeletal thigh muscle, lung, heart, spleen, liver, stomach, small intestine, large intestine, and kidney were collected and weighed. The contents in GI were removed. The radioactivity (total counts in cpm) of the tissue samples was measured directly by gamma counter.

Colon Autoradiography of Diseased and Healthy Mice

Colon radio-autography was performed on colons from Group 0 and Group 2 mice. Colons were harvested, their contents removed, and tissue was exposed to a phosphor-imaging screen (Molecular Dynamics) for 24 hours, and imaged via Storm 860. The results are shown in FIG. 2. Lane-1: colon harvested at 6-hr post injection from Group 0 (healthy mouse); Lane-2: colon harvested at 6-hr post injection from Group 2 (DSS treated mouse); Lane-3: colon harvested at 24-hr post injection from Group 0 (healthy mouse); Lane-4: colon harvested at 24-hr post injection Group 2 (DSS treated mouse). Patchy localization of $^{125}$-F8/IL10 was observed along the colon in the DSS treated mice and not in the normal mice, consistent with the irregular colonic inflammation and associated expression profile of the target EDA in this model.

Determination of Radioactive Equivalent Concentrations in Serum and Tissues and Pharmacokinetic Calculations The serum equivalent concentration (ng eq./g) of $^{125}$-F8/IL10 was estimated based on the measured TCA (trochloroacetic acid) precipitable (protein associated) radioactivity. For TCA precipitation, the aliquot (50 µL) of serum sample was mixed with 50 µL of mouse serum, followed by the addition of 100 µL of 20% TCA solution. The sample mixture was spun at 10,000 g for 5 minutes to precipitate the protein. Total and TCA-soluble radioactivity in the supernatant was determined. TCA-precipitable radioactivity (cpm) in a give sample, the specific activity of the dosing solution (TCA-precipitable cpm per mg of protein), as well as dates of sample ($t_S$) and dosing solution ($t_D$) measurements, were used to calculate the equivalent concentration of test article (ng eq./mL) in a given sample, using the formula: [TCA-precipitable cpm/EXP $(-0.693/60.2*(t_s-t_d))$]/[specific activity (in cpm/mg)*sample volume (in mL)].

The quantitation of equivalent concentration (ng eq./g) of $^{125}$I-F8/IL10 in tissues was calculated based on the measured total radioactivity in the sample and the specific activity of the dosing solution after a correction for physical decay half-life of $^{125}$I, using the formula: [sample cpm/EXP $(-0.693/60.2*(t_S-t_D))$]/[specific activity (in cpm/mg)*sample weight (in mg)]. No homogenization or TCA-precipitation was performed for tissue samples. In addition to radioactive equivalent concentration (ng eq./mL for serum, ne eq./g for tissue), percentage of injected dose per gram (% ID/g) and/or percentage of injected dose (% ID) were also calculated for serum and tissues of interest.

Biodistribution of $^{125}$I-F8/IL10 in normal (Group 0) and DSS treated (Group 1) mice was determined 6 hours (FIG. 3A), 24 hours (FIG. 3B) and 96 hours post-injection (FIG. 3C).

PK parameters were calculated with the mean serum or tissue concentrations at the measured time points. A non-compartmental analysis module of the pharmacokinetic software package WinNonlin (version 5.1 Pharsight) was used. The area under the concentration versus time curve (AUC) was calculated using the linear trapezoidal method.

Effect on Serum Cytokine Levels with Therapeutic Treatment of F8-IL10 in Mouse Model of IBD As IL-10 is know to decrease proinflammatory cytokines, we tested whether administration of F8-IL10 in the mouse model of IBD would affect serum cytokine responses in this model. Mice were administered 200 µg/mouse of F8-IL10, or control small Immune Protein (F8-SIP) IV on day 3, 6 and 9 following initiation of DSS treatment (n=10 mice/group). This dose regimen was the same as effective regimens in collagen induced arthritis models (Schwager K, et al. Arthritis Research and Therapy, (2009) 11: R142). Control groups included non-diseased (regular water) and untreated diseased (n=10 mice/group). On day 10 following initiation of DSS, blood was collected and serum obtained as described above for localizaiton studies. Serum was evaluated for levels of IL-1b, IL-12p40, IFNg, IL-6, KC, IL-10 and TNFa using MSD technology platform and a mouse 7plex MSD kit according to manufacturer's instructions (Mesoscale Discovery, Gaithersburg, Md.). Levels of cytokines are expressed as pg of protein per ml of serum in FIGS. 4 and 5.

Human Tissue Staining for EDA Expression

Immunohistochemical analysis of frozen OCT-embedded specimens of colon tissue of a 60 years old female patient affected by ulcerative colitis and of a 42 years old make patient affected by Chron's disease. Both specimens were probed with the F8 antibody in SIP format and the Von Willebrand factor.

In addition, affected and non-affected frozen biopsy specimens paired from the same patients with Crohn's or ulcerative colitis (n=3 Chron's patients and n=5 UC patients) were obtained from Analytical Biological Services (Wilmington, Del.). Frozen samples were orientated on dry ice to prevent thawing, embedded in Cryomolds, standard (Tissue-Tek 4557) filled with O.C.T. compound (Tissue-Tek #4583) and flash frozen in isopentane that had been cooled by dry ice. The tissue blocks were sectioned on a Leica CM1850 cryostat at 4 microns, placed onto glass slides and stored at −80° C. until the immunohistochemistry (IHC) was performed. Upon initiation of IHC, tissues were dipped in cold (−20 F) methanol (Fisher Scientific A412P-4) to remove any moisture that can form with storage and air dried 20 min at room temperature. Tissues were then dipped into cold (−20 F) acetone (ACROS CAS #67-64-1) for 10 min and air dried 10 min room temperature.

Tissue slides were labeled with appropriate Ventana bar code and placed into a Ventana Discovery XT for Fibronectin F8 SIP or KSF SIP (control antibody) IHC. Endogenous biotin was blocked with both 5% Normal Mouse Serum (Jackson Immuno Research 015-000-120) in Ventana S Block (Ventana 760-4212) for 20 minutes and Ventana Biotin Blocking kit (Ventana 760-050) for 8 minutes. Fibronectin F8SIP or KSF was diluted in Dako antibody diluent (S0908) (Dako North America, Carpinteria, Calif.) at 1:200 concentration (100 ul per slide) and incubated for 40 minutes. Slides were counterstained with hematoxylin and bluing reagent (4 minutes each) before the run was completed. The slides were removed and placed into a Ventana Symphony for subsequent dehydration and coverslipping. Representative images of IHC are shown in FIG. 7. IHC from non-affected (left) and affected (right) tissue samples from ulcerative colitis patient UH0501-34 (top) and Chron's patient UH0405-09 (bottom).

Results

Colon Autoradiography

FIG. 2 shows autoradiography of colons of either non-diseased mice (water) (lanes 1 and 3) or diseased mice (DSS-treated) (lanes 2 and 4) at either 6 (lanes 1 and 2) or 24 (lanes 3 and 4) hours following administration of radiolabeled F8-IL10. This demonstrates that the F8-IL10. This demonstrates that the F8-IL10 does accumulate in the inflamed colon more so than the normal colon. The patchy appearance of the diseased colon localization of the F8-IL10 is consistent with the variable levels of inflammation and EDA expression observed along the length of the colon in this model further supporting localization of F8-IL10 with the inflammation.

Biodistribution of $^{125}$I-F8-IL10 in Diseased and Healthy Mice

Figure 3:
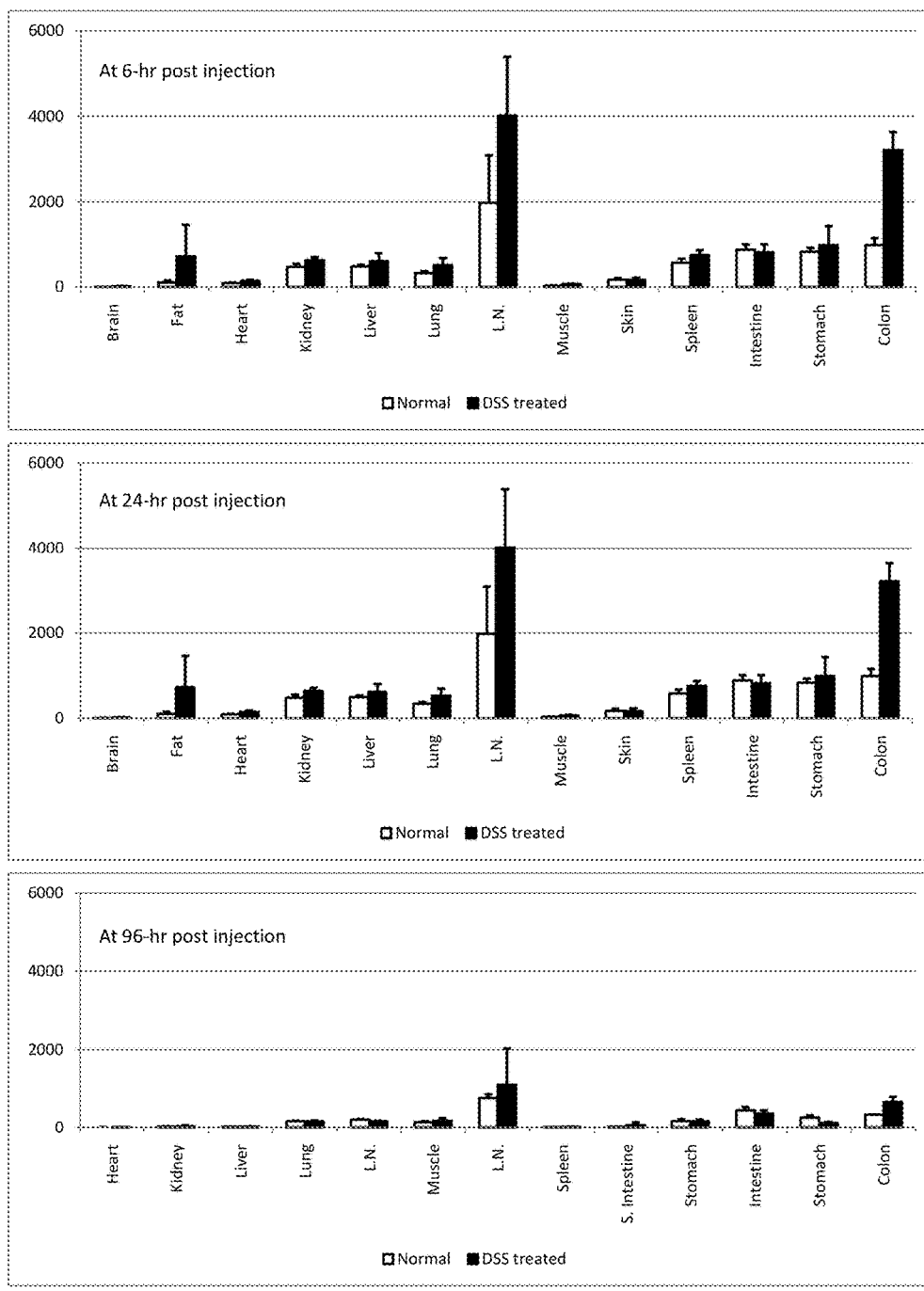
FIG. 3A-3C shows the biodistribution of $^{125}$I-F8-IL10 in healthy or diseased mice. The charts show the biodistribution of $^{125}$I-F8-IL10 in healthy and diseased mice 6 hours post-injection (FIG. 3A) 24 hours post-injection (FIG. 3B) and 96 hours post-injection (FIG. 3C). At 96 hours a preferential accumulation of $^{125}$I-F8-IL10 in the colon and in the mesenteric lymph nodes (L.N.) of diseased mice is visible as compared to healthy mice. The sequence of the F8-IL10 conjugate used in these experiments is shown in SEQ ID NO: 13.

FIG. 3 shows the accumulation of the $^{125}$I-F8-IL10 at 6, 24 and 96 hour time points in the colon and mesenteric lymph nodes (L.N.) in diseased (DSS) mice compared with normal (water) mice. Similar to FIG. 2, these data demonstrate the targeting of F8-IL10 to the colon and associated lymph nodes in DSS-treated mice. Also from these studies, the serum half life was determined to be approximately 3.5 hours whereas the half-life of F8-IL10 in the colon was approximately 35 hours; a 10-fold increase suggesting enhanced tissue persistence. This indicates that not only is F8-IL10 targeting the colon and mesenteric lymph nodes during colonic inflammation, but once there it also persists for longer periods of time than in circulation. Collectively these data suggest that under conditions of inflammation in the colon, such as in Crohn's disease and ulcerative colitis in humans, the F8-IL10 will preferentially target and persist at these sites.

Cytokine Levels in Serum from Diseased and Healthy Mice

FIG. 4 shows that compared to control groups, the administration of F8-IL10 in a therapeutic modality results in a significant decrease in serum levels of inflammatory cytokines, IL-1β, IL12p40, IFNγ and IL-6.

FIG. 5 shows that compared to control groups, the administration of F8-IL10 in a therapeutic modality does not result in an increase of TNF-alpha and Keratinocite derived chemokine (KC) and results in increased levels of IL-10. The increased levels of these cytokines of FIG. 4 in the DSS model are associated with the induction of the disease in the colon. Decreases in these inflammatory cytokines of FIG. 4 and increase in IL-10 are consistent with known biological effects of IL-10 (Abbas A, Lichtman A, Pober J., 1994, Cellular and Molecular Immunology. 2nd Ed. Philadelphia: W. B. Saunders Company; Delves P, Roitt I (eds), 1998, Encyclopedia of Immunology, 2nd Ed. San Diego: Academic Press). Thus, the F8-IL10 demonstrates pharmacological activity in this model of IBD by reducing cytokines associated with inflammation and pathology in the IBD setting. Since these pro-inflammatory cytokines are known to be upregulated in IBD patients, downregulation of these cytokines through administration of F8-IL10 suggests that F8-IL10 is likely to be beneficial in treating IBD in vivo. Interferon γ and IL-12p70, in particular, are known to be upregulated in CD patients, and the data disclosed herein suggest that administration of F8-IL10 is therefore likely to be particularly useful for treating CD in vivo.

Immunohistochemistry

FIG. 6 shows that the F8 SIP antibody stains the newly formed blood vessels but not the normal blood vessels in a patient affected by ulcerative colitis. (Von Willebrand factor is routinely used as a marker of normal vasculature.)

FIG. 7 shows representative images of Crohn's or UC paired biopsy samples stained by immunohistochemistry for EDA. Arrows indicate vessels within each image. The intensity of staining around vessels in the affected vessels is increased compared to unaffected samples from the same patients. This suggests that the increased EDA expression could result in increased targeting to inflamed areas of the colon in these human disease settings. In summary, the colon targeted distribution and decreased serum cytokines observed with F8-IL10 in a murine IBD model as well as the increased expression of EDA around vessels in affected human Crohn's and ulcerative colitis colon tissue collectively provide evidence that suggest that administration of F8-IL10 could target and positively affect patients with IBD.

| SEQUENCES DISCLOSED IN APPLICATION |
| --- |
| SEQ ID NO: 1 (F8 antibody VH domain CDR1) |
| LFT |

SEQUENCES DISCLOSED IN APPLICATION

SEQ ID NO: 2 (F8 antibody VH domain CDR2)
SGSGGS

SEQ ID NO: 3 (F8 antibody VH domain CDR3)
STHLYL

SEQ ID NO: 4 (F8 antibody VL domain CDR1)
MPF

SEQ ID NO: 5 (F8 antibody vl domain CDR2)
GASSRAT

SEQ ID NO: 6 (F8 antibody VL domain CDR3)
MRGRPP

SEQ ID NO: 7 (F8 antibody VH domain)
EVQLLESGGGLVQPGGSLRLSCAASGFTFSLFTMSWVRQAPGKGLEWVSA
ISGSGGSTYYADSVKGRFTISRDNSKNTLYLQMNSLRAEDTAVYYCAKST
HLYLFDYWGQGTLVTVSS SEQ ID NO: 8 (F8 antibody VL domain)
EIVLTQSPGTLSLSPGERATLSCRASQSVSMPFLAWYQQKPGQAPRLLIY
GASSRATGIPDRFSGSGSGTDFTLTISRLEPEDFAVYYCQQMRGRPPTFG
QGTKVEIK SEQ ID NO: 9 (linker between VH domain and VL domain of F8 antibody)
GGSGG SEQ ID NO: 10 (Linker between VL domain of F8 antibody and IL-10)
SSSSGSSSSGSSSSG SEQ ID NO: 11 (human IL-10)
SPGQGTQSENSCTHFPGNLPNMLRDLRDAFSRVKTFFQMKDQLDNLLLKE
SLLEDFKGYLGCQALSEMIQFYLEEVMPQAENQDPDIKAHVNSLGENLKT
LRLRLRRCHRFLPCENKSKAVEQVKNAFNKLQEKGIYKAMSEFDIFINYI
EAYMTMKIRN SEQ ID NO: 12 (F8 antibody)
EVQLLESGGGLVQPGGSLRLSCAASGFTFSLFTMSWVRQAPGKGLEWVSA
ISGSGGSTYYADSVKGRFTISRDNSKNTLYLQMNSLRAEDTAVYYCAKST
HLYLFDYWGQGTLVTVSSGGSGGEIVLTQSPGTLSLSPGERATLSCRASQ
SVSMPFLAWYQQKPGQAPRLLIYGASSRATGIPDRFSGSGSGTDFTLTIS
RLEPEDFAVYYCQQMRGRPPTFGQGTKVEIK SEQ ID NO: 13 (F8-IL10)
EVQLLESGGGLVQPGGSLRLSCAASGFTFSLFTMSWVRQAPGKGLEWVSA
ISGSGGSTYYADSVKGRFTISRDNSKNTLYLQMNSLRAEDTAVYYCAKST
HLYLFDYWGQGTLVTVSSGGSGGEIVLTQSPGTLSLSPGERATLSCRASQ
SVSMPFLAWYQQKPGQAPRLLIYGASSRATGIPDRFSGSGSGTDFTLTIS
RLEPEDFAVYYCQQMRGRPPTFGQGTKVEIKSSSSGSSSSGSSSSGSPGQ
GTQSENSCTHFPGNLPNMLRDLRDAFSRVKTFFQMKDQLDNLLLKESLLE
DFKGYLGCQALSEMIQFYLEEVMPQAENQDPDIKAHVNSLGENLKTLRLR
LRRCHRFLPCENKSKAVEQVKNAFNKLQEKGIYKAMSEFDIFINYIEAYM
TMKIRN

The invention claimed is:

1. A method of treating inflammatory bowel disease (IBD) in a patient, the method comprising administering to a patient a therapeutically effective amount of an antibody conjugate,
wherein the antibody conjugate comprises an antibody, or an antigen-binding fragment thereof, that binds the Extra Domain-A (ED A) of fibronectin conjugated to human interleukin-10 (IL-10), wherein the antibody or antigen-binding fragment comprises a $V_H$ domain and a $V_L$ domain,
wherein the $V_H$ domain comprises the heavy chain complementarity determining region (HCDR) 1, HCDR2, and HCDR3 amino acid sequences in SEQ ID NO: 7; and
wherein the $V_L$ domain comprises the light chain complementarity determining region (LCDR) 1, LCDR2, and LCDR3 amino acid sequences in SEQ ID NO: 8.

2. The method of claim 1, wherein the antibody or antigen-binding fragment is conjugated to the IL-10 by a cleavable linker.

3. The method of claim 1, wherein the $V_H$ domain framework is a human germline framework.

4. The method of claim 3, wherein the $V_H$ domain has the amino acid sequence of SEQ ID NO: 7.

5. The method of claim 1, wherein the $V_L$ domain framework is a human germline framework.

6. The method of claim 5, wherein the $V_L$ domain has the amino acid sequence of SEQ ID NO: 8.

7. The method of claim 1, wherein the antigen-binding fragment comprises a single chain Fv.

8. The method of claim 7, wherein the antigen-binding fragment is a small immunoprotein (SIP).

9. The method of claim 1, wherein the IBD is not ulcerative colitis (UC).

10. The method of claim 9, wherein the antibody conjugate comprises the amino acid sequence of SEQ ID NO: 13.

11. The method of claim 1, wherein the IBD is selected from the group consisting of: collagenous colitis, lymphocytic colitis, ischaemic colitis, diversion colitis, Behget's disease, indeterminate colitis, and Crohn's disease.

12. The method of claim 11, wherein the antibody conjugate comprises the amino acid sequence of SEQ ID NO: 13.

13. The method of claim 1, wherein the $V_H$ and $V_L$ domains are conjugated to each other via an amino acid linker.

14. The method of claim 13, wherein the amino acid linker consists of the amino acid sequence of SEQ ID NO: 9.

15. The method of claim 1, wherein the antibody or antigen-binding fragment is conjugated to the IL-10 via a peptide linker comprising the amino acid sequence of SEQ ID NO: 10.

16. The method of claim 1, wherein the antibody conjugate comprises the amino acid sequence of SEQ ID NO: 13.

* * * * *

SEQUENCE LISTING

<160> NUMBER OF SEQ ID NOS: 13

<210> SEQ ID NO 1
<211> LENGTH: 3
<212> TYPE: PRT
<213> ORGANISM: Artificial Sequence
<220> FEATURE:
<223> OTHER INFORMATION: F8 antibody VH domain CDR1

<400> SEQUENCE: 1

Leu Phe Thr
 1

<210> SEQ ID NO 2
<211> LENGTH: 6
<212> TYPE: PRT
<213> ORGANISM: Artificial Sequence
<220> FEATURE:
<223> OTHER INFORMATION: F8 antibody VH domain CDR2

<400> SEQUENCE: 2

Ser Gly Ser Gly Gly Ser
 1               5

<210> SEQ ID NO 3
<211> LENGTH: 6
<212> TYPE: PRT
<213> ORGANISM: Artificial Sequence
<220> FEATURE:
<223> OTHER INFORMATION: F8 antibody VH domain CDR3

<400> SEQUENCE: 3

Ser Thr His Leu Tyr Leu
 1               5

<210> SEQ ID NO 4

```
<211> LENGTH: 3
<212> TYPE: PRT
<213> ORGANISM: Artificial Sequence
<220> FEATURE:
<223> OTHER INFORMATION: F8 antibody VL domain CDR1

<400> SEQUENCE: 4

Met Pro Phe
 1

<210> SEQ ID NO 5
<211> LENGTH: 7
<212> TYPE: PRT
<213> ORGANISM: Artificial Sequence
<220> FEATURE:
<223> OTHER INFORMATION: F8 antibody VL domain CDR2

<400> SEQUENCE: 5

Gly Ala Ser Ser Arg Ala Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: F8 antibody VL domain CDR3

<400> SEQUENCE: 6

Met Arg Gly Arg Pro Pro
 1               5

<210> SEQ ID NO 7
<211> LENGTH: 118
<212> TYPE: PRT
<213> ORGANISM: Artificial Sequence
<220> FEATURE:
<223> OTHER INFORMATION: F8 antibody VH domain

<400> SEQUENCE: 7

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Leu Phe
                20                  25                  30

Thr Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
                100                 105                 110

Leu Val Thr Val Ser Ser
            115

<210> SEQ ID NO 8
<211> LENGTH: 108
<212> TYPE: PRT
<213> ORGANISM: Artificial Sequence
<220> FEATURE:
<223> OTHER INFORMATION: F8 antibody VL domain
```

<400> SEQUENCE: 8

| Glu | Ile | Val | Leu | Thr | Gln | Ser | Pro | Gly | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Gln | Ser | Val | Ser | Met | Pro |
|---|---|---|---|---|---|---|---|---|---|---|---|---|---|---|---|
| | | | 20 | | | | | 25 | | | | | 30 | | |

| Phe | Leu | Ala | Trp | Tyr | Gln | Gln | Lys | Pro | Gly | Gln | Ala | Pro | Arg | Leu | Leu |
|---|---|---|---|---|---|---|---|---|---|---|---|---|---|---|---|
| | | 35 | | | | | 40 | | | | | 45 | | | |

| Ile | Tyr | Gly | Ala | Ser | Ser | Arg | Ala | Thr | Gly | Ile | Pro | Asp | Arg | Phe | Ser |
|---|---|---|---|---|---|---|---|---|---|---|---|---|---|---|---|
| 50 | | | | | 55 | | | | | 60 | | | | | |

| Gly | Ser | Gly | Ser | Gly | Thr | Asp | Phe | Thr | Leu | Thr | Ile | Ser | Arg | Leu | Glu |
|---|---|---|---|---|---|---|---|---|---|---|---|---|---|---|---|
| 65 | | | | 70 | | | | | 75 | | | | | 80 | |

| Pro | Glu | Asp | Phe | Ala | Val | Tyr | Tyr | Cys | Gln | Gln | Met | Arg | Gly | Arg | Pro |
|---|---|---|---|---|---|---|---|---|---|---|---|---|---|---|---|
| | | | | 85 | | | | | 90 | | | | | 95 | |

| Pro | Thr | Phe | Gly | Gln | Gly | Thr | Lys | Val | Glu | Ile | Lys |
|---|---|---|---|---|---|---|---|---|---|---|---|
| | | | 100 | | | | | 105 | | | |

<210> SEQ ID NO 9
<211> LENGTH: 5
<212> TYPE: PRT
<213> ORGANISM: Artificial Sequence
<220> FEATURE:
<223> OTHER INFORMATION: linker between VH domain and VL domain of F8
    antibody

<400> SEQUENCE: 9

| Gly | Gly | Ser | Gly | Gly |
|---|---|---|---|---|
| 1 | | | | 5 |

<210> SEQ ID NO 10
<211> LENGTH: 15
<212> TYPE: PRT
<213> ORGANISM: Artificial Sequence
<220> FEATURE:
<223> OTHER INFORMATION: Linker between VL domain of F8 antibody and
    IL-10

<400> SEQUENCE: 10

| Ser | Ser | Ser | Ser | Gly | Ser | Ser | Ser | Gly | Ser | Ser | Ser | Gly |
|---|---|---|---|---|---|---|---|---|---|---|---|---|
| 1 | | | | 5 | | | | | 10 | | | | | 15 |

<210> SEQ ID NO 11
<211> LENGTH: 160
<212> TYPE: PRT
<213> ORGANISM: Homo sapiens

<400> SEQUENCE: 11

| Ser | Pro | Gly | Gln | Gly | Thr | Gln | Ser | Glu | Asn | Ser | Cys | Thr | His | Phe | Pro |
|---|---|---|---|---|---|---|---|---|---|---|---|---|---|---|---|
| 1 | | | | 5 | | | | | 10 | | | | | 15 | |

| Gly | Asn | Leu | Pro | Asn | Met | Leu | Arg | Asp | Leu | Arg | Asp | Ala | Phe | Ser | Arg |
|---|---|---|---|---|---|---|---|---|---|---|---|---|---|---|---|
| | | | 20 | | | | | 25 | | | | | 30 | | |

| Val | Lys | Thr | Phe | Phe | Gln | Met | Lys | Asp | Gln | Leu | Asp | Asn | Leu | Leu | Leu |
|---|---|---|---|---|---|---|---|---|---|---|---|---|---|---|---|
| | | 35 | | | | | 40 | | | | | 45 | | | |

| Lys | Glu | Ser | Leu | Leu | Glu | Asp | Phe | Lys | Gly | Tyr | Leu | Gly | Cys | Gln | Ala |
|---|---|---|---|---|---|---|---|---|---|---|---|---|---|---|---|
| | 50 | | | | | 55 | | | | | 60 | | | | |

| Leu | Ser | Glu | Met | Ile | Gln | Phe | Tyr | Leu | Glu | Glu | Val | Met | Pro | Gln | Ala |
|---|---|---|---|---|---|---|---|---|---|---|---|---|---|---|---|
| 65 | | | | | 70 | | | | | 75 | | | | | 80 |

| Glu | Asn | Gln | Asp | Pro | Asp | Ile | Lys | Ala | His | Val | Asn | Ser | Leu | Gly | Glu |
|---|---|---|---|---|---|---|---|---|---|---|---|---|---|---|---|
| | | | | 85 | | | | | 90 | | | | | 95 | |

| Asn | Leu | Lys | Thr | Leu | Arg | Leu | Arg | Leu | Arg | Arg | Cys | His | Arg | Phe | Leu |
|---|---|---|---|---|---|---|---|---|---|---|---|---|---|---|---|
| | | | 100 | | | | | 105 | | | | | 110 | | |

```
Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
        130                 135                 140

Ile Phe Ile Asn Tyr Ile Glu Ala Tyr Met Thr Met Lys Ile Arg Asn
145                 150                 155                 160

<210> SEQ ID NO 12
<211> LENGTH: 231
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Ser Gly Gly Glu Ile Val Leu Thr
        115                 120                 125

Gln Ser Pro Gly Thr Leu Ser Leu Ser Pro Gly Glu Arg Ala Thr Leu
    130                 135                 140

Ser Cys Arg Ala Ser Gln Ser Val Ser Met Pro Phe Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Arg Leu Glu Pro Glu Asp Phe Ala
        195                 200                 205

Val Tyr Tyr Cys Gln Gln Met Arg Gly Arg Pro Pro Thr Phe Gly Gln
    210                 215                 220

Gly Thr Lys Val Glu Ile Lys
225                 230

<210> SEQ ID NO 13
<211> LENGTH: 406
<212> TYPE: PRT
<213> ORGANISM: Artificial Sequence
<220> FEATURE:
<223> OTHER INFORMATION: F8-IL10

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30
```

-continued

```
Thr Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Ser Thr His Leu Tyr Leu Phe Asp Tyr Trp Gly Gln Gly Thr
            100                 105                 110
Leu Val Thr Val Ser Ser Gly Gly Ser Gly Gly Glu Ile Val Leu Thr
        115                 120                 125
Gln Ser Pro Gly Thr Leu Ser Leu Ser Pro Gly Glu Arg Ala Thr Leu
    130                 135                 140
Ser Cys Arg Ala Ser Gln Ser Val Ser Met Pro Phe Leu Ala Trp Tyr
145                 150                 155                 160
Gln Gln Lys Pro Gly Gln Ala Pro Arg Leu Leu Ile Tyr Gly Ala Ser
                165                 170                 175
Ser Arg Ala Thr Gly Ile Pro Asp Arg Phe Ser Gly Ser Gly Ser Gly
            180                 185                 190
Thr Asp Phe Thr Leu Thr Ile Ser Arg Leu Glu Pro Glu Asp Phe Ala
        195                 200                 205
Val Tyr Tyr Cys Gln Gln Met Arg Gly Arg Pro Pro Thr Phe Gly Gln
    210                 215                 220
Gly Thr Lys Val Glu Ile Lys Ser Ser Ser Gly Ser Ser Ser Ser Ser
225                 230                 235                 240
Gly Ser Ser Ser Gly Ser Pro Gly Gln Gly Thr Gln Ser Glu Asn
                245                 250                 255
Ser Cys Thr His Phe Pro Gly Asn Leu Pro Asn Met Leu Arg Asp Leu
            260                 265                 270
Arg Asp Ala Phe Ser Arg Val Lys Thr Phe Phe Gln Met Lys Asp Gln
        275                 280                 285
Leu Asp Asn Leu Leu Leu Lys Glu Ser Leu Leu Glu Asp Phe Lys Gly
    290                 295                 300
Tyr Leu Gly Cys Gln Ala Leu Ser Glu Met Ile Gln Phe Tyr Leu Glu
305                 310                 315                 320
Glu Val Met Pro Gln Ala Glu Asn Gln Asp Pro Asp Ile Lys Ala His
                325                 330                 335
Val Asn Ser Leu Gly Glu Asn Leu Lys Thr Leu Arg Leu Arg Leu Arg
            340                 345                 350
Arg Cys His Arg Phe Leu Pro Cys Glu Asn Lys Ser Lys Ala Val Glu
        355                 360                 365
Gln Val Lys Asn Ala Phe Asn Lys Leu Gln Glu Lys Gly Ile Tyr Lys
    370                 375                 380
Ala Met Ser Glu Phe Asp Ile Phe Ile Asn Tyr Ile Glu Ala Tyr Met
385                 390                 395                 400
Thr Met Lys Ile Arg Asn
                405
```